United States Patent
Yu et al.

(10) Patent No.: US 10,426,363 B2
(45) Date of Patent: Oct. 1, 2019

(54) MAGNETOENCEPHALOGRAPHY MEASURING APPARATUS

(71) Applicant: KOREA RESEARCH INSTITUTE OF STANDARDS AND SCIENCE, Daejeon (KR)

(72) Inventors: Kwon-Kyu Yu, Daejeon (KR); Yong-Ho Lee, Daejeon (KR); Kiwoong Kim, Daejeon (KR); Jin-Mok Kim, Daejeon (KR); Hyukchan Kwon, Daejeon (KR); Sang-Kil Lee, Daejeon (KR)

(73) Assignee: Korea Research Institute of Standards and Science, Daejeon (KR)

( * ) Notice: Subject to any disclaimer, the term of this patent is extended or adjusted under 35 U.S.C. 154(b) by 742 days.

(21) Appl. No.: 15/059,939

(22) Filed: Mar. 3, 2016

(65) Prior Publication Data

US 2016/0174862 A1 Jun. 23, 2016

Related U.S. Application Data

(63) Continuation of application No. PCT/KR2014/008049, filed on Aug. 29, 2014.

(30) Foreign Application Priority Data

Sep. 11, 2013 (KR) ........................ 10-2013-0108872

(51) Int. Cl.
*A61B 5/04* (2006.01)
*A61B 5/05* (2006.01)
(Continued)

(52) U.S. Cl.
CPC ........ *A61B 5/04008* (2013.01); *A61B 5/0522* (2013.01); *A61B 5/6803* (2013.01);
(Continued)

(58) Field of Classification Search
CPC ...... A61B 2562/0223; A61B 2562/046; A61B 5/04008; A61B 5/0522; A61B 5/6803; A61B 5/6814; G01R 33/0354
See application file for complete search history.

(56) References Cited

U.S. PATENT DOCUMENTS

| 5,495,849 A | 3/1996 | Hayashi et al. |
| 7,729,740 B2 | 6/2010 | Kraus, Jr. et al. |

(Continued)

FOREIGN PATENT DOCUMENTS

| JP | H05 42119 A | 2/1993 |
| JP | 2009-045198 A | 3/2009 |

OTHER PUBLICATIONS

IPRP and Written Opinion for Application No. PCT/KR2014/008049 dated Mar. 15, 2016.
(Continued)

*Primary Examiner* — Ruth S Smith
(74) *Attorney, Agent, or Firm* — Jenkins, Wilson, Taylor & Hunt, P.A.

(57) ABSTRACT

A magnetoencephalography (MEG) measuring apparatus and an MEG measuring method. The MEG measuring apparatus includes a superconducting helmet having an inward brim, a sensor-equipped helmet disposed inside the superconducting helmet, a pick-up coil disposed inside the sensor-equipped helmet, and a superconducting quantum interference device (SQUID) sensor mounted on the sensor-equipped helmet and connected to the pick-up coil.

16 Claims, 20 Drawing Sheets

(51) Int. Cl.
*A61B 5/00* (2006.01)
*G01R 33/035* (2006.01)

(52) U.S. Cl.
CPC ........ *A61B 5/6814* (2013.01); *G01R 33/0354* (2013.01); *A61B 2562/0223* (2013.01); *A61B 2562/046* (2013.01)

(56) References Cited

U.S. PATENT DOCUMENTS

| | | |
|---|---|---|
| 8,456,164 B2 | 6/2013 | Subbarao |
| 2005/0234329 A1 | 10/2005 | Kraus, Jr. et al. |
| 2005/0272996 A1* | 12/2005 | Matsui ............... A61B 5/04008 600/409 |
| 2012/0126811 A1 | 5/2012 | Subbarao |
| 2014/0005518 A1* | 1/2014 | Ko .................... A61B 5/04008 600/409 |
| 2014/0121491 A1* | 5/2014 | Zhang ............... A61B 5/04008 600/409 |

OTHER PUBLICATIONS

International Search Report for Application No. PCT/KR2014/008049 dated Dec. 18, 2014.
Korean Office Action for Korean Application No. 10-2013-0108872 dated Dec. 18, 2014.
Grant of Patent for Korean Application No. 10-2013-0108872 dated Mar. 4, 2015.

* cited by examiner

MAGNETOENCEPHALOGRAPHY MEASURING APPARATUS

CROSS-REFERENCE TO RELATED APPLICATIONS

This application is a continuation of and claims priority to PCT/KR2014/008049 filed on Aug. 29, 2014, which claims priority to Korea Patent Application No. 10-2013-0108872 filed on Sep. 11, 2013, the entireties of which are both hereby incorporated by reference herein.

TECHNICAL FIELD

The present disclosure relates to magnetoencephalography measuring apparatuses and, more particularly, to a magnetoencephalography measuring apparatus having a superconducting shielding structure.

BACKGROUND

A person's brain has many brain nerve cells, and a magnetoencephalography (hereinafter referred to as "MEG") signal is generated by ionic electrical activity of the brain nerve cells. If an MEG signal is measured, medical applications such as diagnosis of brain functions, localization of an epilepsy developing location, and cognitive function diagnosis are made possible. However, an MEG signal generated from a brain is a very weak signal of tens to hundreds of femto-Tesla (fT). A high-sensitivity magnetic sensor and technical development capable of effectively shielding earth's magnetic field and environmental noise are required to detect such a weak signal with a high signal-to-noise ratio (SNR).

A superconducting quantum interference device (hereinafter referred to as "SQUID") sensor using a superconductor is a magnetic sensor having very high sensitivity and is necessarily used in an MEG signal measuring system. A SQUID sensor needs to be connected to a pick-up coil to measure a magnetic signal with the SQUID sensor. According to types of pick-up coils, SQUID sensors are classified into a magnetometer adapted to measure a magnetic field value and a gradiometer adapted to measure spatial differential of a magnetic field.

A method for removing environmental magnetic noise includes a method for fabricating a signal pick-up coil in the form of a gradiometer and a method for mounting a magnetically shielded room (MSR) using a metal having high permeability and a metal having high electrical conductivity. Moreover, the environmental magnetic noise may be additionally removed through the procedure of processing a measured signal.

When a pick-up coil is fabricated in the form of a gradiometer, a first-order gradiometer is generally introduced. In this case, spatially non-uniform noise may not be removed effectively or a reference channel may reduce a signal to cause SNR reduction. Magnetic shielding using a magnetically shielded room may effectively shield a magnetic field but requires a long fabrication time and a wide fabrication space. In addition, since magnetic shielding must use a metal having high electrical conductivity such as Permalloy, much cost is required. To overcome these disadvantages, various studies have been conducted on magnetic shielding using Meissner effect that is a characteristic where a magnetic field cannot penetrate a superconductor under a superconducting state. Superconducting shield has constant shielding performance according to a frequency and is an ideally perfect shielding method.

When a superconductor is implemented in the form of a helmet using superconducting shielding characteristics, a superconducting helmet may suppress a noise from a low frequency to a high frequency due to superconducting shielding effect in the superconducting helmet. In particular, when a conventional magnetically shielded room is used, many high-priced Permalloys must be used to obtain a high shielding factor in a low-frequency region of 0.1 Hz or less. However, in case of superconducting shield, a high shielding factor may be obtained even in the low-frequency region of 0.1 Hz or less.

According to superconducting shielding theory, when a magnetic signal source $M_{source}$ is disposed at a position spaced apart by a distance "a" in a direction perpendicular to a superconductor plane, current flowing to a superconducting shielding material surface, a virtual magnetic signal source $M_{image}$ of the same size but an opposite direction is likely to exist opposite to the magnetic signal source $M_{source}$. Therefore, theoretically, a gradiometer spaced part from a superconductor surface by the distance "a" operates the same as a primary gradiometer whose base line is "2a", which was proved by the Los Alamos National Laboratory (LANL) study group.

Thus, when a superconductor is fabricated in the form of a helmet, magnetic shielding may be achieved in a superconducting helmet. According to depth of a signal source desired to be measured, spaced distance between a superconductor material surface and a pick-up coil may be adjusted to determine length of a base line. In addition, the superconducting shield may provide a constant shielding effect according to a frequency. The LANL study group announced the effectiveness of superconducting shield by manufacturing an MEG apparatus in the form of a shielding helmet directly cooled with liquid helium and measuring a shielding factor depending on each position of a gradiometer in the helmet and a somatosensory signal.

However, according to a result of the LANL study group, a signal-to-noise ratio of a gradiometer disposed at the edge of an MEG helmet was lower than when superconducting shielding is not performed. The reduction in the signal-to-noise ratio of the gradiometer disposed at the edge of the MEG helmet is caused by the fact that density of a magnetic-force line increased at the edge of the helmet. An MEG signal was actually measured depending on whether superconducting shielding is performed. When the superconducting shielding was performed, a somatosensory signal near a vertex was measured to have a high signal-to-noise ratio whereas an evoked signal for an auditory cortex and a visual cortex reacting at left and right temporal regions and an occipital region had a very low signal-to-noise ratio. In particular, when superconducting shielding was performed, a cardiac magnetic signal and an interest vibration noise of a measurement person were measured to be very high and great at the edge of a superconducting shielding helmet. The significant increase in external noise intensity is caused by magnetic field focusing effect at the edge of the superconducting shielding helmet.

Referring to U.S. Pat. No. 7,729,740, to overcome the above problem, the LANL study group mounted a reference magnetometer for measuring only an environmental magnetic noise outside a superconducting shielding helmet and applied an adaptive filter to remove the noise. However, when the adaptive filter is used, the inside of the superconducting shield and an external nose must have the same frequency and the same frequency element. In addition, when the noise element is much greater than a signal element desired to be measured, the application of the adaptive filter is not effective. In particular, a magnetic signal generated from a person's heart is detected by a magnetometer inside the helmet but is not often detected by a reference magnetometer. Accordingly, there is a need for a novel superconducting shielding structure to improve a shielding effect at the edge of a helmet.

SUMMARY

Embodiments of the present disclosure provide an economical magnetoencephalography (MEG) measuring apparatus which measures an MEG signal having an excellent signal-to-noise ratio (SNR) by using a superconducting shield.

A magnetoencephalography (MEG) measuring apparatus according to an example embodiment of the present disclosure includes a superconducting helmet having an inward brim, a sensor-equipped helmet disposed inside the superconducting helmet, a pick-up coil disposed inside the sensor-equipped helmet, and a superconducting quantum interference device (SQUID) sensor mounted on the sensor-equipped helmet and connected to the pick-up coil.

In an example embodiment, the superconducting helmet, the sensor-equipped helmet, the pick-up coil, and the SQUID sensor may be submerged in a liquid refrigerant to be directly cooled.

In an example embodiment, the pick-up coil may be a magnetometer.

In an example embodiment, width of the inward brim may be 20 to 40 mm.

In an example embodiment, the superconducting helmet may further include an outward brim, a hemispherical portion, a cylindrical straight portion successively connected to the hemispherical portion, and a visual field ensuring portion where the straight portion is partially removed. The inward brim may be disposed along an inner side surface from a bottom surface of the straight portion and be in the form of a washer removed in a direction of the visual field ensuring portion. The outward brim may be disposed along an outer side surface from the bottom surface of the straight portion and be in the form of the washer removed in the direction of the visual field ensuring portion.

In an example embodiment, the superconducting helmet may further include an inward side brim disposed at opposite sides of the visual field ensuring portion and connected to the inward brim, an outward side brim disposed at the opposite sides of the visual field ensuring portion and connected to the outward brim, an inward upper brim disposed on the visual field ensuring portion and connected to the inward side brim, and an outward upper brim disposed on the visual field ensuring portion and connected to the outward side brim.

In an example embodiment, a material of the superconducting helmet may be lead.

In an example embodiment, the pick-up coil may be disposed to have a constant vertical direction on an inner side of the sensor-equipped helmet and the vertical direction may be equal to the width of the inward brim.

A magnetoencephalography (MEG) measuring apparatus according to an example embodiment of the present disclosure include an inner container adapted to store a liquid refrigerant and including an inner helmet, an outer container including an outer helmet disposed to surround the inner helmet, a superconducting helmet disposed in a space between the inner helmet and the outer helmet and including an inward brim, a sensor-equipped helmet disposed in a space between the superconducting helmet and the outer helmet, a pick-up coil disposed in a space between the sensor-equipped helmet and the outer helmet, and a superconducting quantum interference device (SQUID) sensor mounted on the sensor-equipped helmet and connected to the pick-up coil. A space between the inner container and the outer container may be maintained in a vacuum state.

In an example embodiment, the pick-up coil may be a magnetometer.

In an example embodiment, width of the inward brim may be 20 to 40 mm.

In an example embodiment, the superconducting helmet may further include an outward brim, a hemispherical portion, a cylindrical straight portion successively connected to the hemispherical portion, and a visual field ensuring portion where the straight portion is partially removed. The inward brim may be disposed along an inner side surface from a bottom surface of the straight portion and be in the form of a washer removed in a direction of the visual field ensuring portion. The outward brim may be disposed along an outer side surface from the bottom surface of the straight portion and be in the form of the washer removed in the direction of the visual field ensuring portion.

In an example embodiment, the superconducting helmet may further include an inward side brim disposed at opposite sides of the visual field ensuring portion and connected to the inward brim, an outward side brim disposed at the opposite sides of the visual field ensuring portion and connected to the outward brim, an inward upper brim disposed on the visual field ensuring portion and connected to the inward side brim, and an outward upper brim disposed on the visual field ensuring portion and connected to the outward side brim.

In an example embodiment, a spaced distance from an inner surface of a superconducting helmet to the pick-up coil may be equal to the width of the inward brim.

In an example embodiment, the MEG measuring apparatus may further include a thermal cap disposed between the sensor-equipped helmet and the outer helmet.

A magnetoencephalography (MEG) measuring method according to an example embodiment of the present disclosure includes vertically providing an external magnetic field on a disposition plane of a pick-up coil disposed to be vertically and constantly spaced apart from an inner side surface of a superconducting helmet including an inward brim and measuring an MEG signal using the pick-up coil and a superconducting quantum interference device (SQUID) sensor.

In an example embodiment, the pick-up coil and the SQUID sensor may be disposed in vacuum.

In an example embodiment, a spaced distance from an inner surface of a superconducting helmet to the pick-up coil may be equal to width of the inward brim.

A magnetoencephalography (MEG) measuring apparatus according to an example embodiment of the present disclosure includes a superconducting helmet having an inward brim, a sensor-equipped helmet disposed inside the superconducting helmet, and a superconducting quantum interference device (SQUID) sensor disposed inside the sensor-equipped helmet.

BRIEF DESCRIPTION OF THE DRAWINGS

The present disclosure will become more apparent in view of the attached drawings and accompanying detailed description. The embodiments depicted therein are provided by way of example, not by way of limitation, wherein like reference numerals refer to the same or similar elements. The drawings are not necessarily to scale, emphasis instead being placed upon illustrating aspects of the present disclosure.

DETAILED DESCRIPTION

Figure 1:
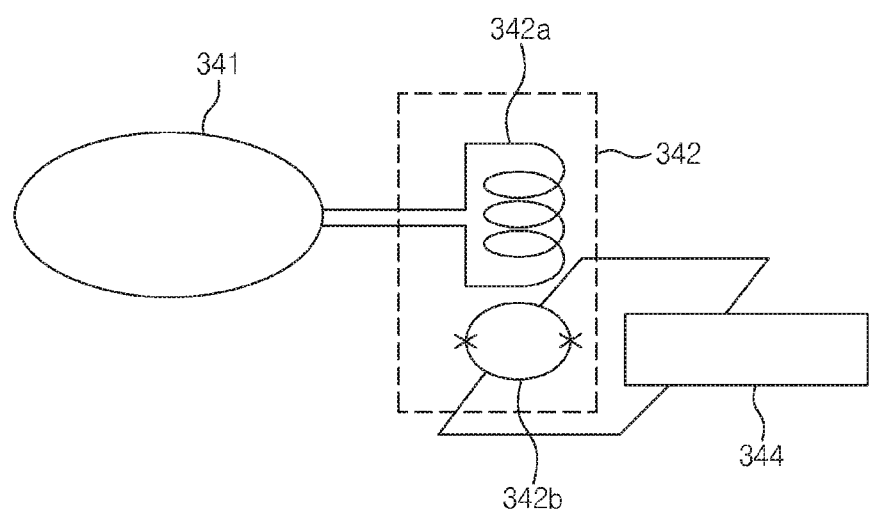
FIG. 1 is a conceptual diagram of measuring a magnetic field using a SQUID and a pick-up coil.

According to an example embodiment of the present disclosure, a magnetoencephalography (hereinafter referred to as "MEG") apparatus using helmet-type superconducting shield may be fabricated, which may operate in a low-priced magnetically shielded room. Thus, similar to the LANL study group (U.S. Pat. No. 7,729,740), an auditory evoked signal may be measured without using a reference magnetometer and an adaptive filter. A signal-to-noise ratio (SNR) of the measured signal was compared according to a superconducting shielding structure. Through a result of the comparison, usefulness of a superconducting shielding-type apparatus according to the present disclosure was confirmed. That is, a superconducting helmet having a bidirectional brim was proposed to remove influx of great magnetic field noise caused by a magnetic field focusing effect at the edge of helmet-type superconducting shield and the effect of the superconducting helmet was confirmed.

Example embodiments will now be described more fully with reference to the accompanying drawings, in which some example embodiments are shown. Example embodiments may, however, be embodied in many different forms and should not be construed as being limited to the embodiments set forth herein; rather, these example embodiments are provided so that this disclosure will be thorough and complete, and will fully convey the scope of example embodiments of inventive concepts to those of ordinary skill in the art. In the drawings, the thicknesses of layers and regions are exaggerated for clarity. Like reference characters and/or numerals in the drawings denote like elements, and thus their description may be omitted.

[Type of Superconducting Shield and Shielding Effect Comparison Depending on Distance Variation]

FIG. 1 is a conceptual diagram of measuring a magnetic field using a SQUID and a pick-up coil.

Referring to FIG. 1, a SQUID sensor module may include a pick-up coil 341 and a SQUID sensor 342. The SQUID sensor 342 may include an input coil 342a and a SQUID 342b. The SQUID sensor 342 may be connected to a circuit unit 344. The pick-up coil 341 may include a G-10 epoxy rod and an NbTi wire covering the epoxy rod. The input coil 342a of the SQUID sensor 342 and the pick-up coil 341 may be connected with each other through an Nb wire using a sonic wedge bonder.

A superconducting shielding material employed a lead (Pb) plate having purity of 99.95 percent and thickness of 0.5 mm.

To confirm the shielding effect at a helmet-type superconducting shielding structure, a magnetic field was applied to a helmet using a coil having a Helmholtz structure and a shielding factor was measured and compared according to a brim structure and a position of the SQUID sensor 342 inside the helmet.

A magnetic shielding factor is defined as below:

$$\text{Shielding Factor}(S) = \frac{H^{(0)}}{H_{axial}} \quad \text{Equation (1)}$$

wherein $H^{(0)}$ represents the intensity of an external magnetic field and, $H_{axial}$ represents the intensity of an axial magnetic field.

[Magnetic Field Distribution for Design of Optimal Superconducting Shielding Helmet and Magnetic-Force Line Direction Simulation]

When a superconducting shielding helmet is fabricated, a magnetic-force line expelled from the center of a shielding material is focused on the edge to make flux density of the edge higher than when the edge is not shielded. In addition, an incident angle of the magnetic-force line to a pick-up coil spaced to be perpendicular to a superconducting shielding surface increase. Thus, a detected flux (=B A sin θ) increases (B being the intensity of the magnetic field, A being an area of the pick-up coil, and θ being an angle between the magnetic field and a normal line of the pick-up coil). For this reason, magnetic noise of the SQUID sensor disposed at the edge of the helmet further increases due to the superconducting shield. In a test, a perfect conductor model was applied to the superconducting shield and magnetic field analysis was simulated using Maxwell 3D.

A Helmholtz coil was designed to be sufficiently larger than the helmet to establish a uniform magnetic field. The Helmholtz coil was used to establish a uniform external magnetic field. A radius of the Helmholtz was 500 mm, a coil spacing was 500 mm, the winding number of coil was one turn, and applied current is 100 ampere (A). The designed coil established a magnetic field of about 250 μT in its center.

The shape of the helmet edge was changed to understand an influence of external noise on a SQUID sensor module. First, a virtual test was performed on a helmet having a unidirectional brim. Second, a brim was formed in both directions to optimize a magnetic field distribution and a magnetic-force line direction at a position where a pick-up coil of the SQUID sensor was disposed. In case of a bidirectional brim, length or width of an outwardly formed brim was 50 mm and length or width of an inwardly formed brim was 30 mm. A perpendicularly spaced distance between a superconducting shielding surface and the pick-up coil was designed to be equal to the width of the inwardly formed brim. That is, the length or the width of the inwardly formed brim is made equal to the perpendicularly spaced distance of the pick-up coil to minimize an incident angle of a magnetic-force line that is incident on the pick-up coil.

[Manufacturing of Superconducting Shielding Helmet-Type MEG Apparatus]

Three types of inserts were designed and fabricated to confirm characteristics depending on a shape of a superconducting shielding helmet-type MEG apparatus.

A first insert is an MEG insert including a gradiometer pick-up coil having a conventional base line of 50 mm, a second insert is a superconducting shielding helmet-type MEG insert having an outward brim, and a third insert is a superconducting shielding helmet-type MEG insert having an inward brim and an outward brim. With a fabricated MEG insert, an external noise influence and signal characteristics were evaluated in the same cooling apparatus.

Figure 2:
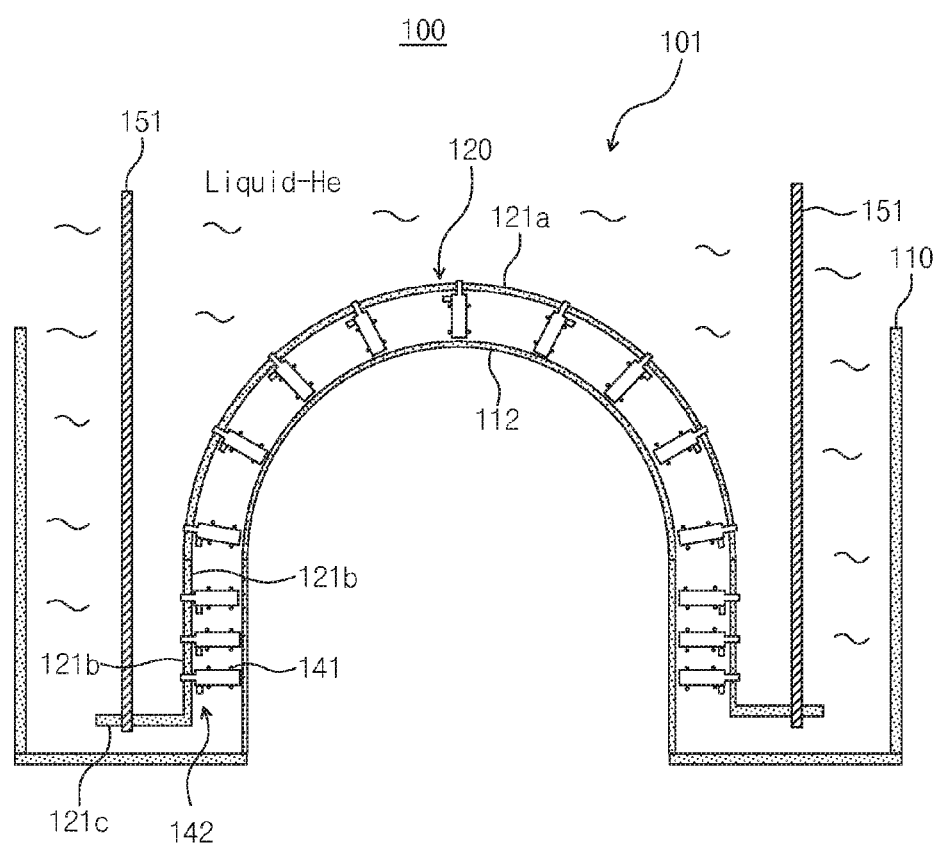
FIG. 2 illustrates a conventional magnetoencephalography (MEG) measuring apparatus using a SQUID gradiometer as a magnetic field detection sensor.

FIG. 2 illustrates a conventional magnetoencephalography (MEG) measuring apparatus 100 using a SQUID gradiometer as a magnetic field detection sensor.

Referring to FIG. 2, a first insert 101 includes a gradiometer. The first insert 101 does not use superconducting shield. The first insert 101 is submerged in a liquid refrigerant of an inner container 110 of a Dewar to be cooled. A pick-up coil 141 employed a wire-wound gradiometer. The pick-up coil 141, where a signal coil and a reference coil are wound in opposite direction, includes a pair of coils spaced apart from each other in a fixed distance. A length of a base line between the signal coil and the reference coil is 50 mm. The number of pick-up coils 141 uniformly mounted on a surface of a sensor-equipped helmet 120 is 152. The pick-up coil 141 and the SQUID sensor 142 may be fabricated and integrated into a single module to be wound on the liquid refrigerant.

The sensor-equipped helmet 120 may include a hemispherical portion 121a, a cylindrical straight portion 121b successively connected to the hemispherical portion 121a, and a washer-shaped brim 121c extending from a bottom surface to the outside of the straight portion 121b. The brim 121c may be connected to an insert body (not shown) through a support rod 151. The insert body may include a plurality of insert baffles to prevent evaporation of the refrigerant.

Since the first insert 101 is sensitive to external environmental noise, the first insert 101 requires a magnetically shielded room (MSR). Even when the magnetically shielded room is used, many high-priced Permalloys must be used because it is difficult to magnetically shield a low-frequency element.

Figure 3:
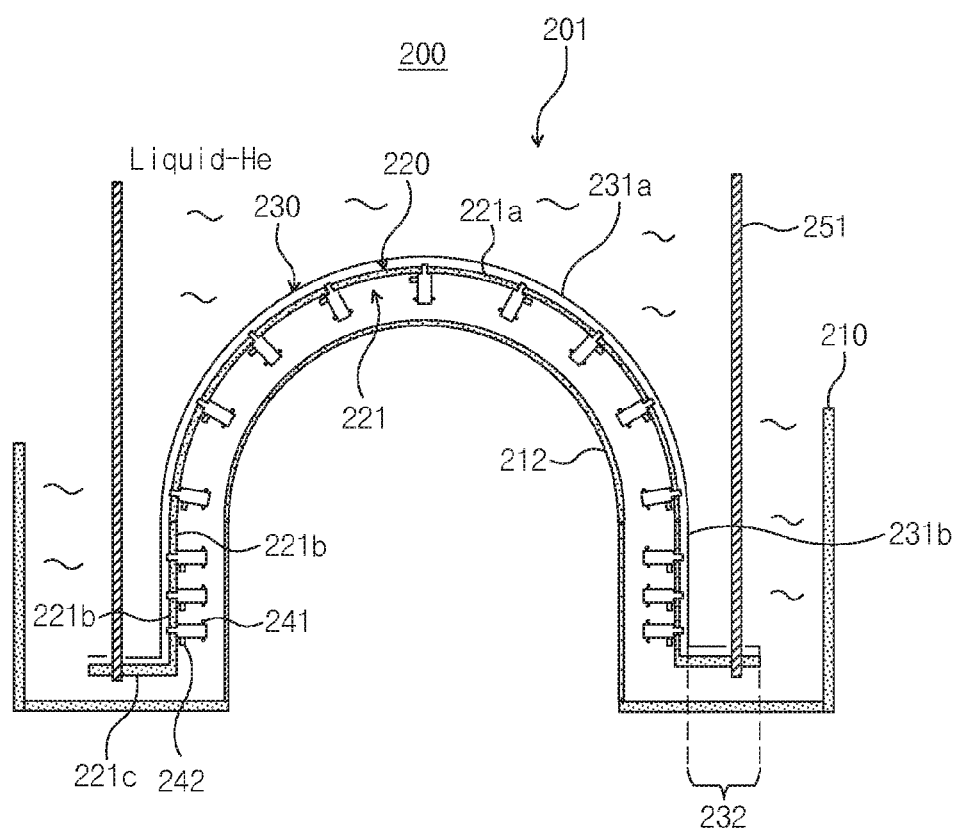
FIG. 3 illustrates a superconducting shielding helmet-type magnetoencephalography (MEG) measuring apparatus having an outward brim structure.

FIG. 3 illustrates a superconducting shielding helmet-type magnetoencephalography (MEG) measuring apparatus 200 having an outward brim structure.

Referring to FIG. 2, a second insert 201 may include a superconducting shielding helmet 230 having an outward brim structure. The superconducting shielding helmet 230 of the outward brim structure was fabricated using a lead plate having purity of 99.95 percent. A sensor-equipped helmet 220 is mounted inside the superconducting shielding helmet 230.

A pick-up coil 241 employs a magnetometer. The number of pick-up coils 241 uniformly mounted on a surface of the sensor-equipped helmet 220 is 152. The pick-up coil 241 may include a bobbin and a one-turn NbTi wire covering the bobbin. The pick-up coil 241 and a SQUID sensor 242 may be fabricated and integrated into a single module to be disposed at the sensor-equipped helmet 220. The sensor-equipped helmet 220 is connected to an insert body (not shown) through a support rood 251. The superconducting shielding helmet 230 and the sensor-equipped helmet 220 are submerged in a liquid refrigerant to be cooled.

In case of a superconducting shielding helmet-type MEG manufacturing apparatus having an outward brim, fifteen reference SQUID sensor channels (not shown) at five points in a three-dimensional vector manner to use an adaptive filter. The reference SQUID sensor channel (not shown) is disposed outside the superconducting shielding helmet 230.

The superconducting shielding helmet 230 includes a hemispherical portion 231a, a cylindrical straight portion 231b successively connected to the hemispherical portion 231a, and a washer-shaped outward brim 232 extending from a bottom surface to the outside of the straight portion 231b.

The superconducting shielding helmet-type MEG measuring apparatus 200 having an outward brim may reduce weight of a magnetically shielded room. However, the superconducting shielding helmet-type MEG measuring apparatus 200 having an outward brim requires a conventional SQUID sensor channel. In addition, the superconducting shielding helmet-type MEG measuring apparatus 200 having an outward brim does not measure well an MEG signal generated at an auditory cortex or a visual cortex in the vicinity of the edge of the superconducting helmet. Thus, a superconducting helmet having another structure is required to measure the MEG signal generated at the auditory cortex or the visual cortex.

Figure 4A:
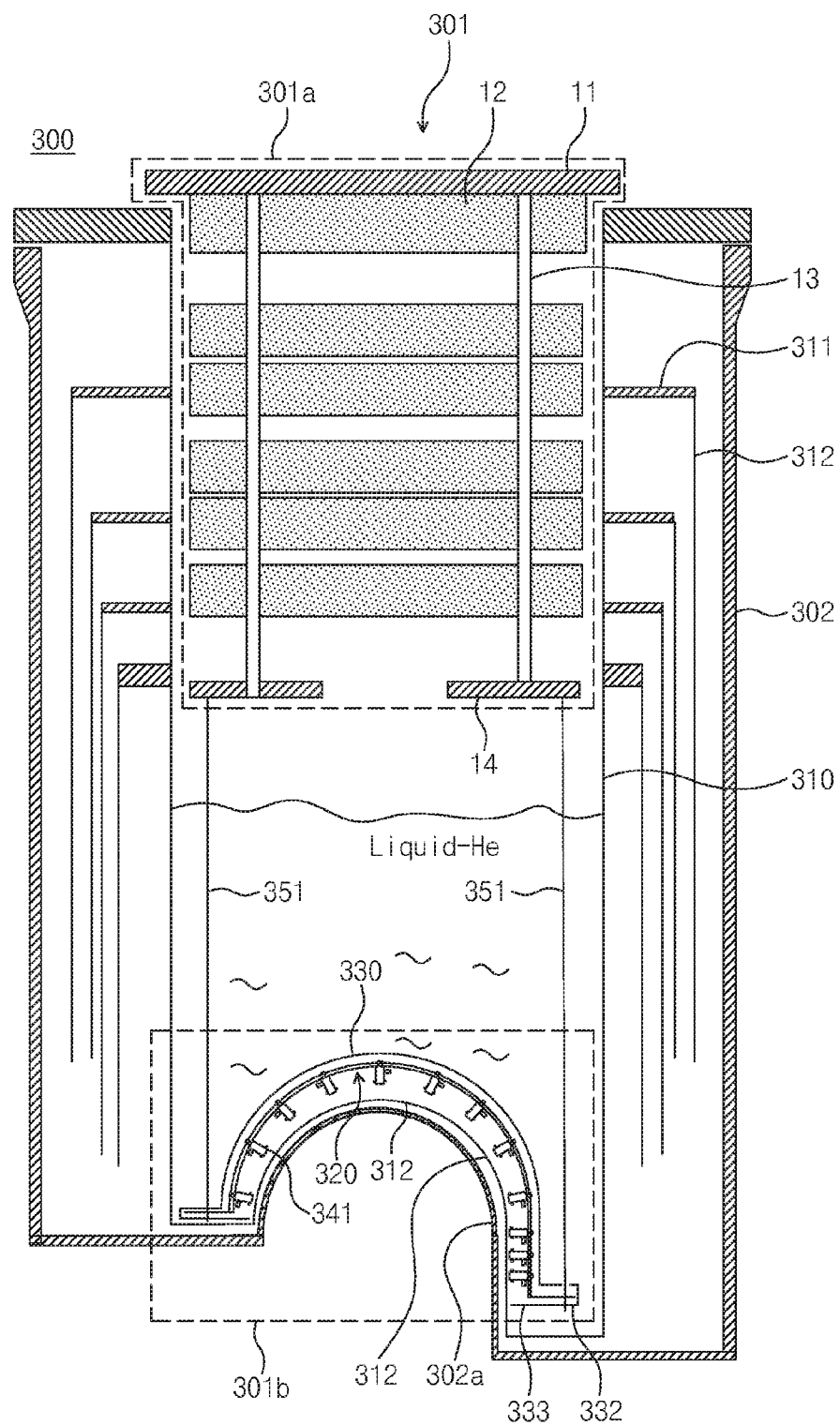
FIG. 4A illustrates a superconducting shielding helmet-type magnetoencephalography (MEG) apparatus having a bidirectional brim structure according to an example embodiment of the present disclosure.

FIG. 4A illustrates a superconducting shielding helmet-type magnetoencephalography (MEG) apparatus having a bidirectional brim structure according to an example embodiment of the present disclosure.

Figure 4B:
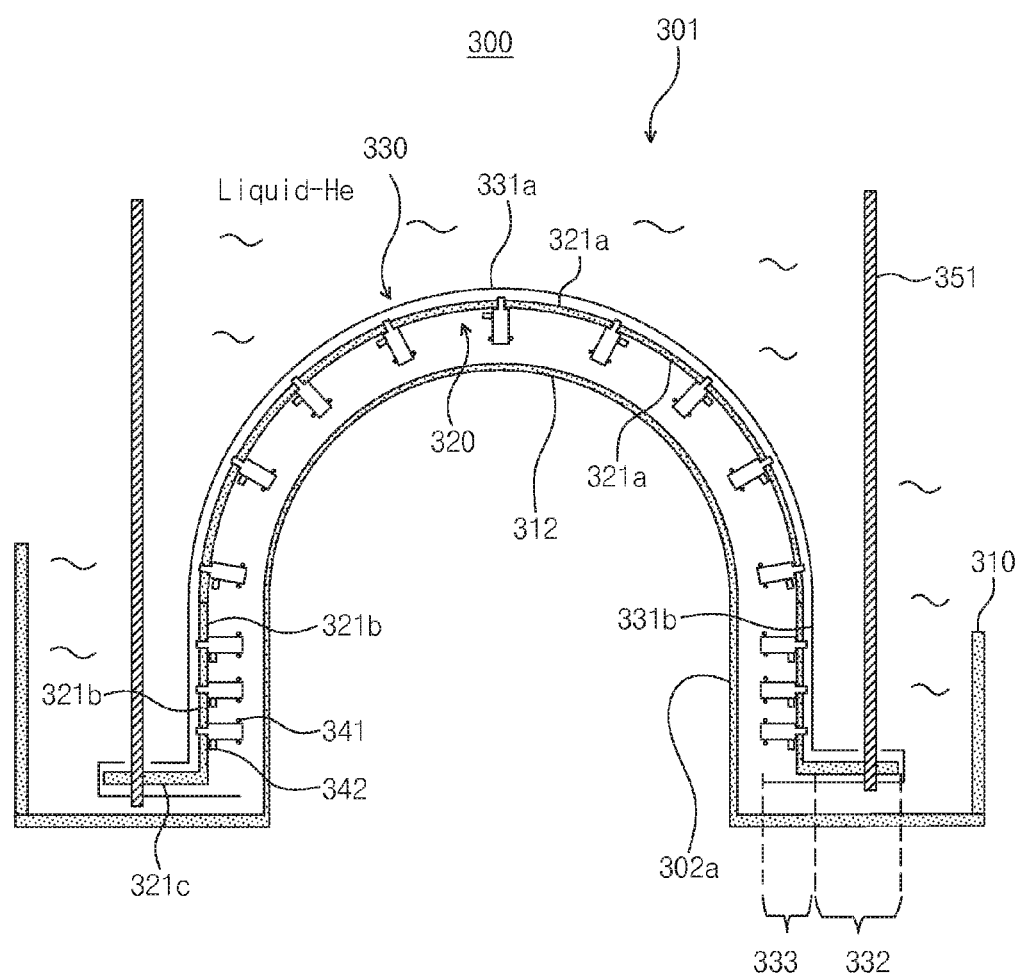
FIG. 4B illustrates a superconducting shielding helmet-type insert having the bidirectional brim structure in FIG. 4A.

FIG. 4B illustrates a superconducting shielding helmet-type insert having the bidirectional brim structure in FIG. 4A.

Figure 4C:
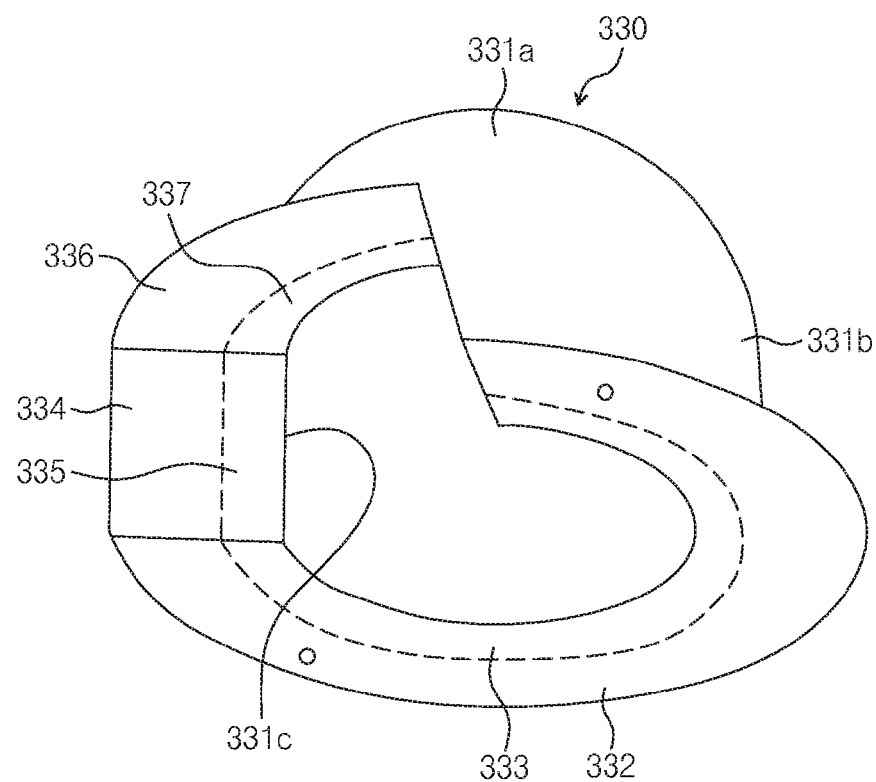
FIG. 4C is an exploded perspective view of a superconducting shielding helmet and a sensor-equipped helmet.
Figure 4C:
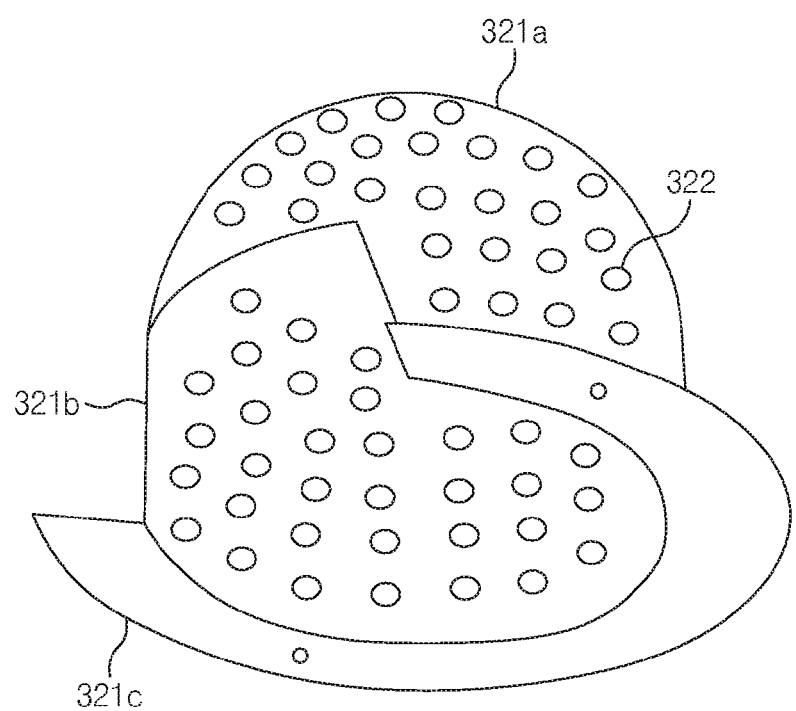

FIG. 4C is an exploded perspective view of a superconducting shielding helmet and a sensor-equipped helmet.

Referring to FIGS. 4A through 4C, a third insert 301 may include a superconducting shielding helmet 330 of a bidirectional brim structure. A lead plate having purity of 99.95 percent was fabricated in the form of a helmet to use helmet-type MEG in superconducting shield. A sensor-equipped helmet 320 is mounted inside the superconducting shielding helmet 330. A pick-up coil 341 employed a magnetometer. The number of pick-up coils 341 uniformly mounted on a surface of the sensor-equipped helmet 320 was 152. The SQUID sensor 342 and the pick-up coil 341 are fabricated and integrated into a single module to be mounted on the sensor-equipped helmet 320. A magnetometer may include a bobbin and a one-turn NbTi wire covering the bobbin.

During connection between the SQUID sensor 342 and the pick-up coil 341, an aid such an Nb plate and an Nb screw was not used and direct bonding was performed for integration of an MEG apparatus. This integration results in the advantage that stray inductance between the pick-up coil 341 and the SQUID sensor 342 may decrease to about one-tenth to significantly improve a balance factor. An Nb wire used in the bonding was thermally treated in vacuum at temperature of 1900 degrees centigrade to increase ductility of the Nb wire. The superconducting shield employs a sonic wedge bonder. The SQUID sensor 342 was fixed to a sensor fixing block attached to the sensor-equipped helmet 320 by using a plastic screw.

A magnetoencephalography (MEG) measuring apparatus 300 according to an example embodiment of the present disclosure includes a superconducting helmet 330 having an inward brim 333, a sensor-equipped helmet 320 disposed inside the superconducting helmet 330, a pick-up coil disposed inside the sensor-equipped helmet 320, and a SQUID 342 mounted on the sensor-equipped helmet 320 and connected to the pick-up coil 341.

A Dewar may include an inner container 310 and an outer container 302. The Dewar may have a coaxial cylindrical structure. A space between the outer container 302 and the inner container 310 may be maintained at a vacuum state. The outer container 302 may include a top plate. A through-hole may be formed in the center of the top plate. The inner container 310 may be connected to the through-hole. The outer container 302 may have a cylindrical shape. An external helmet 302a may be disposed on a bottom surface of the outer container 302 to allow a person's head to be inserted.

The inner container 310 may be in the form of a lidless cylinder. An inner helmet 312 aligned with the outer helmet 302 may be disposed on a bottom surface of the inner container 310. A washer-shaped support 311 may be disposed on an outer surface of the inner container 310. A thermal shielding part 312 may be disposed on an outer circumferential surface of the inner container 310. The thermal shielding part 312 may include an upper cylindrical portion and a lower slit portion successively connected to the upper cylindrical portion. The lower slit portion may have a slit that is perpendicularly formed. The thermal shielding part 312 may be made of a conductive material. A liquid refrigerant may be stored in the inner container 310.

An insert 301 may include an insert body 301a and a measurement portion 301b connected to the insert body 301a. The insert 301 may be inserted into the inner container 310 to perform an adiabatic function. The insert body 301a may include an insert top plate 11, a guide rod 13 combined with the insert top plate 11 and extending vertically, an insert baffle 12 inserted into the guide rod 13, a support plate 14 for fixing the sensor-equipped helmet 320, and a support rod 351 connecting the support plate 114 and the sensor-equipped helmet 320 with each other.

The insert top plate 11 may be in the form of a disc and be made of G-10 epoxy. The insert top plate 11 may be fixed to a top plate of the outer container 302.

The guide rod 13 may be made of G-10 epoxy and be in the form of a rod or a pipe. The guide rod 13 may be means for supporting the insert baffle 12.

The insert baffle 12 may include a Styrofoam with superior warmth retention and a conductive plate. The conductive plate may include an aluminum-coated Mylar layer and a copper layer. The insert baffle 12 may block external thermal conductivity and influx of radiant heat.

The support plate 14 may be made of G-10 epoxy and be in the form of a washer. The support plate 14 may fix the sensor-equipped helmet 320 through the support rod 351.

The support rod 351 may be made of G-10 epoxy and be in the form of a rod. The support rod 351 may be provided in plurality, be connected to the support plate 14, and extend perpendicularly to be connected to the sensor-equipped helmet 320.

The sensor-equipped helmet 320 includes a hemispherical portion 321a, a cylindrical straight portion 321b successively connected to the hemispherical portion 321a, and an outward brim connected to a bottom surface of the straight portion in an outward direction. The straight portion 321b may be partially removed in a direction that a person' eye views. A plurality of through-holes 322 may be formed at the straight portion 321b and the hemispherical portion 321a of the sensor-equipped helmet 320. A SQUID sensor module is mounted in the through-hole 322.

The sensor-equipped helmet 320 may be made of G-10 epoxy and be fabricated with a plurality of components using an epoxy adhesive. The hemispherical portion 321a may have a hemispherical shape. The shape of the hemispherical portion 321a may be variously modified into, for example, a parabolic shape or an elliptical shape allowing a person's head to be inserted. The straight portion 321b may be successively connected to the hemispherical portion 321a. Accordingly, the straight portion 321b may have a cylindrical shape. The shape of the straight portion 321b is not limited to the cylindrical shape, and the straight portion 321b may have a greater radius of curvature than the hemispherical portion 321a. The straight portion 321b may be partially removed to provide a visual field ensuring portion. Specifically, an azimuthal element having the range between 45 and 180 degrees may be removed. Thus, a person's eye may ensure a visual field when the person's head is inside the sensor-equipped helmet 320. The outward brim may have a washer shape.

The superconducting helmet 330 includes an inward brim 333, an outward brim 332, a hemispherical portion 331, a cylindrical straight portion 331b successively connected to the hemispherical portion 331a, and a visual field ensuring portion 331c where the straight portion 331b is partially removed. The superconducting helmet 330 may further include an inward side brim 335 disposed at opposite sides of the visual field ensuring portion 331c and connected to the inward brim 333, an outward side brim 334 disposed at opposite sides of the visual field ensuring portion 331c and connected to the outward brim 332, an inward upper brim 337 disposed on the visual field ensuring portion 331c and connected to the inward side brim 335, and an outward upper brim 336 disposed on the visual field ensuring portion 331c and connected to the outward side brim 334. The superconducting helmet 330 may shield external magnetic noise to measure an MEG signal when performance of a magnetically shielded from is degraded or the magnetically shielded room does not exist.

The inward brim 333, the inward side brim 335, and the inward upper brim 337 may be successively connected. The outward brim 332, the outward side brim 334, and the outward upper brim 336 may be successively connected. Length or width of the inward brim may be about 20 mm to about 40 mm. A material of the superconducting helmet 330 may be lead (Pb). The superconducting helmet 330 may be fabricated by folding a plate or using a mold. The outward brim 332 of the superconducting helmet 330 may be disposed to cover the outward brim 321c of the sensor-equipped helmet 320.

To compare signal characteristics and external environmental noise characteristics, three types of measurement inserts were evaluated in a magnetically shielded room using the same circuit and the same Dewar. Characteristics of the used magnetically shielded room employed aluminum having high electrical conductivity and a magnetic material having high initial permeability. A magnetic shielding factor of the fabricated magnetically shielded room was 140 times (@0.1 Hz) and 80,000 times (@100 Hz). To measure a magnetic field signal, a SQUID circuit may include a flux-locked-loop (FLL) circuit using a normal front-end amplifier and an analog signal processing circuit ASP for noise filter and amplification of a measured signal. The analog signal processing circuit may include a low-pass filter (100 Hz), a high-pass filter (0.1 Hz), a 60 Hz notch filter, and a 40 dB amplifier.

[Measurement and Comparison of Noise Characteristics and Signal Characteristics of Meg System According to Superconducting Shield]

To evaluate characteristics of a system according to a superconducting shielding structure, system noise distribution, magnetic field signal distribution for the same magnetic field, and an auditory evoked signal for the same measurement target were measured using the same magnetically shield room and the same measurement circuit. By opening residual noise in the magnetically shielded room and a door of the magnetically shielded room, a system noise distribution and a noise spectrum for three types of superconducting shielding structures were measured under a weak magnetic shielding state.

When the same external magnetic field was applied, a variation and a distribution of the magnetic field were measured according to a shape and a position of a superconducting shielding structure in a helmet. To reliably compare a magnetic field noise distribution and a signal variation characteristic according to a shape of each system, a SQUID sensor was selected and used in each system to have the same characteristics. The used SQUID sensor was limited to have driving current (35 to 40 uA), a modulation voltage (80 to 90 uV), and white noise (2.5 to 3.5 fT/Hz$^{1/2}$). An auditory evoked signal for a pure tone (500 Hz, 1 kHz) of a healthy man was measured 100 times. A signal-to-noise ratio (SNR) of the measured signal was compared according to the superconducting shielding structure.

[Shielding Factor Variation Depending on Shape of Superconducting Shield]

To confirm shielding characteristics according to superconducting shield, a hemispherical shielding structure having a diameter of 130 mm and depth of 60 mm was fabricated and a shielding factor was measured according to a distance from a surface of the superconducting shield. A high shielding factor of about 700 times was exhibited at a distance of 5 mm from a hemispherical inner bottom, and the shielding factor decreased exponentially as the distance increased. Accordingly, a shielding characteristic of about 100 times was exhibited at a spaced distance of 45 mm.

Figure 5:
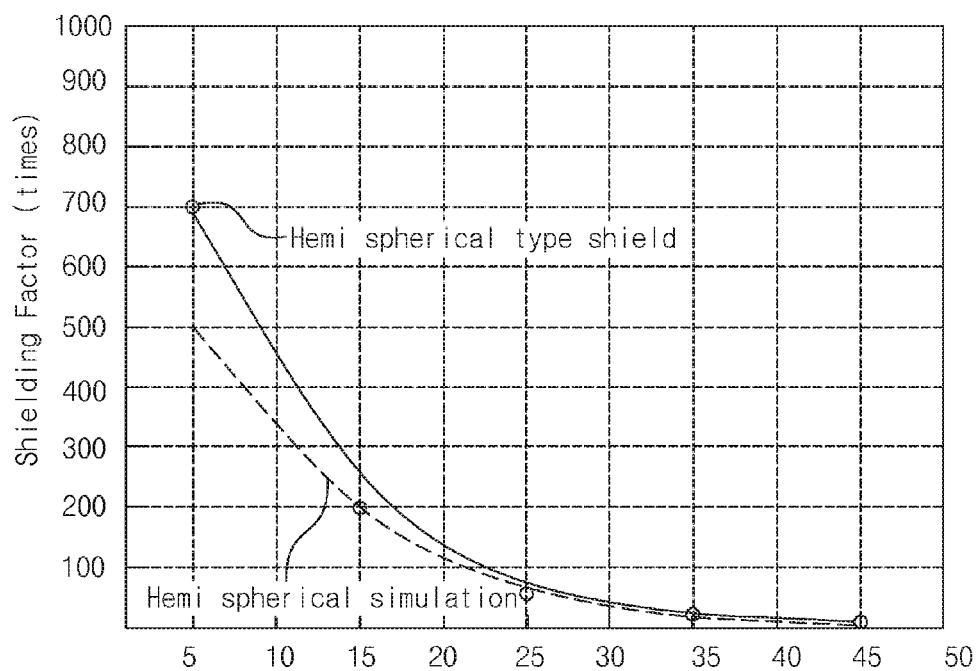
FIG. 5 illustrates shielding factor variation depending on a distance from a superconducting shielding surface.

FIG. 5 illustrates shielding factor variation depending on a distance from a superconducting shielding surface.

According to an example embodiment of the present disclosure, a SQUID sensor and a pick-up coil are fabricated and integrated into a single module to maintain a vertically spaced distance between a surface of a superconductor and the pick-up coil within the range of 20 mm to 40 mm.

There is a need for a structure design of a superconducting helmet for measuring a wide-area acknowledge signal generated at an auditory cortex and a visual cortex while keeping the vertically spaced distance of the surface of the superconductor and the pick-up coil within the range of 20 mm to 40 mm.

[Design of Optimized Superconducting Shielding Helmet-Type MEG Insert]

To measure a magnetoencephalography (MEG) signal, 152 SQUID sensors were disposed on a helmet surface at regular intervals. When there is no superconducting shield, an externally introduced magnetic field may impinge on a pick-up coil without distortion of a magnetic-force line at a position where each of the SQUID sensors is disposed. Meanwhile, when there is superconducting shield, a distribution of an externally introduced magnetic field and a direction of a magnetic-force line are distorted according to a shape of a helmet. Thus, a redistribution and a magnetic-force line of a uniform external magnetic field were analyzed to receive the external magnetic field least at a position where a pick-up coil of a SQUID sensor is disposed and design an optimized shape of a superconducting shielding helmet which is capable of minimizing variation of a signal source.

Figure 6A:
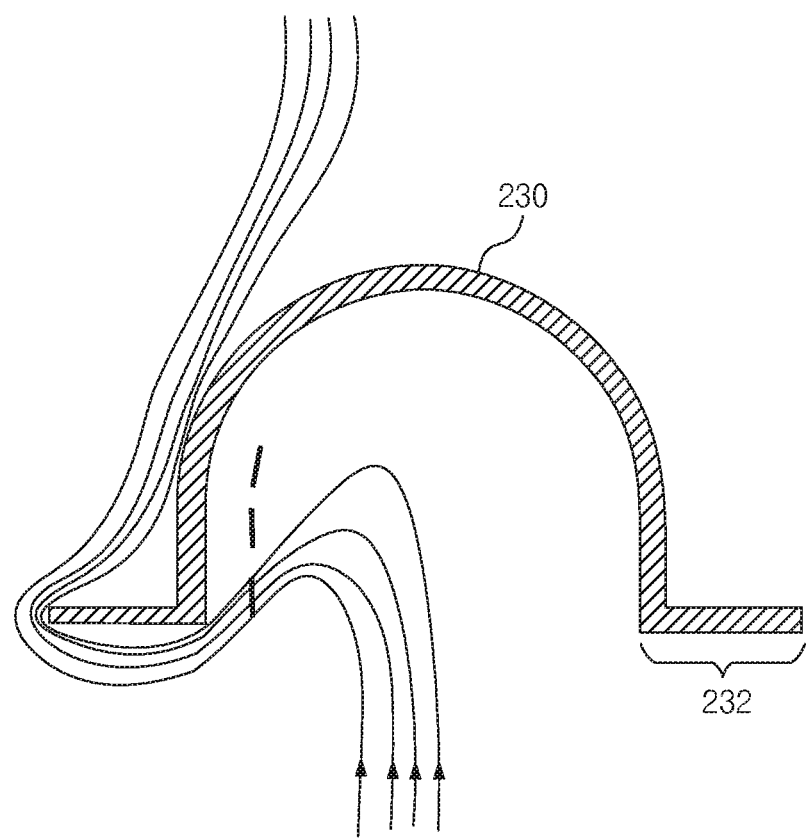
FIGS. 6A and 6B conceptually illustrate a magnetic-force line direction in a superconducting shielding helmet structure according to a brim type of a helmet.
Figure 6B:
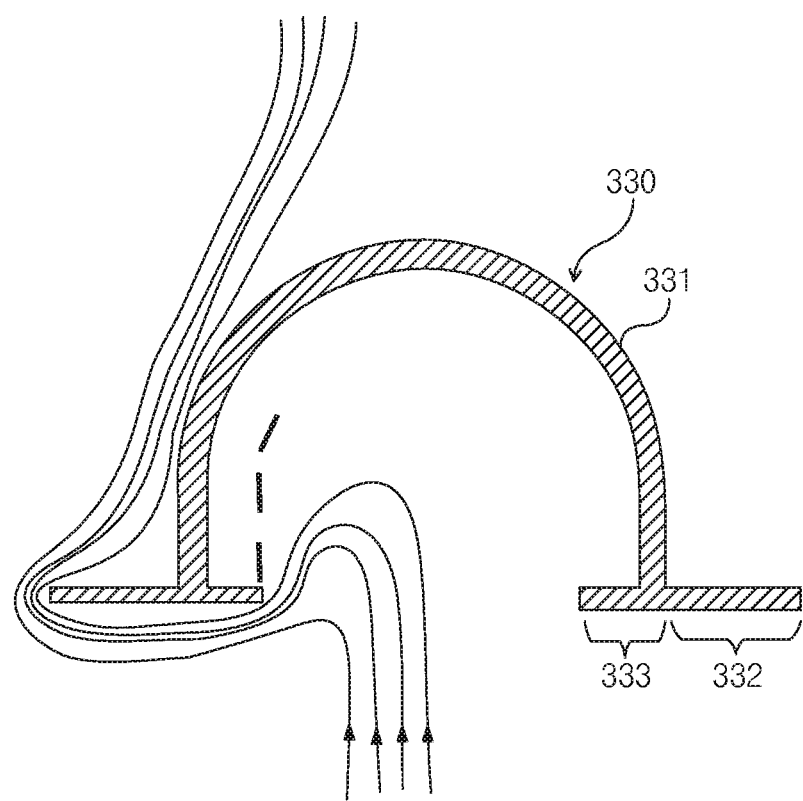

FIGS. 6A and 6B conceptually illustrate a magnetic-force line direction in a superconducting shielding helmet structure according to a brim type of a helmet.

Figure 7A:
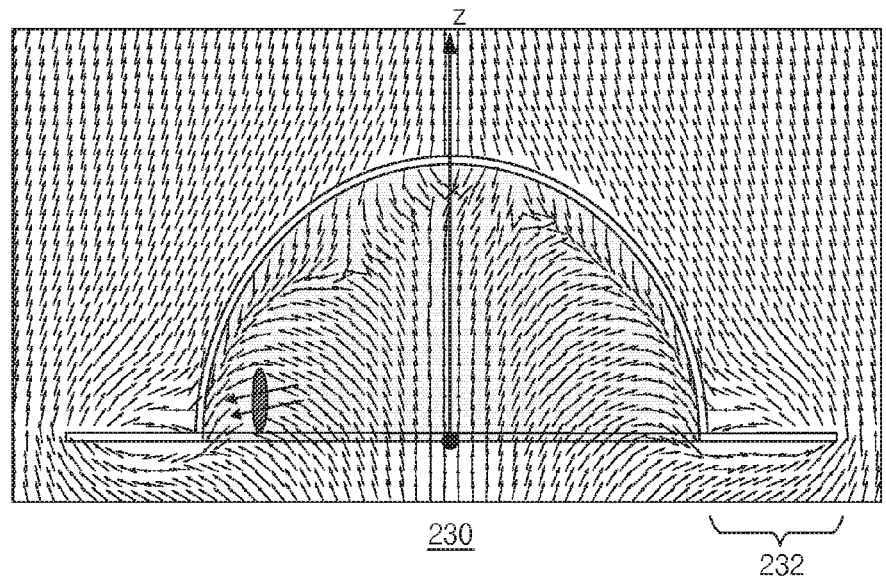
FIGS. 7A and 7B illustrate simulation results of a magnetic-force line direction in a superconducting shielding helmet structure according to a brim type of a helmet.
Figure 7B:
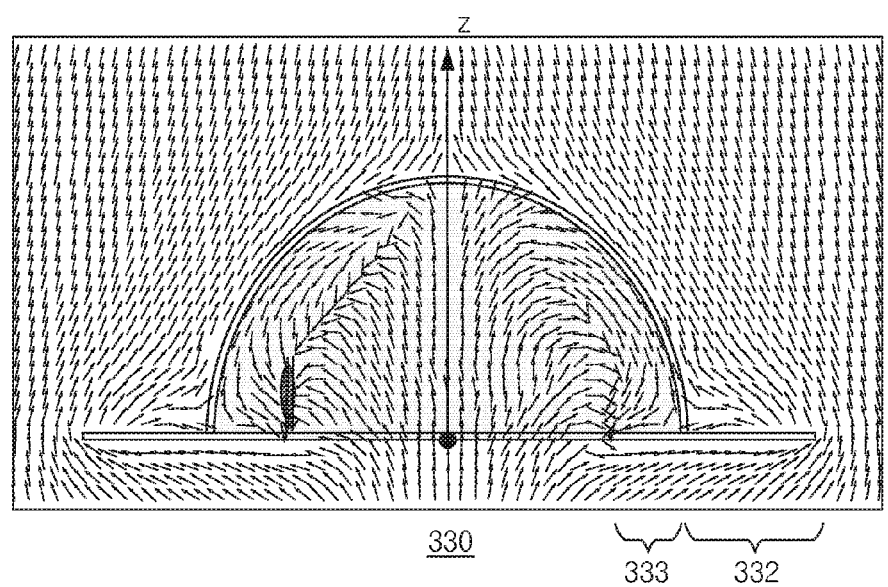

FIGS. 7A and 7B illustrate simulation results of a magnetic-force line direction in a superconducting shielding helmet structure according to a brim type of a helmet.

Figure 8A:
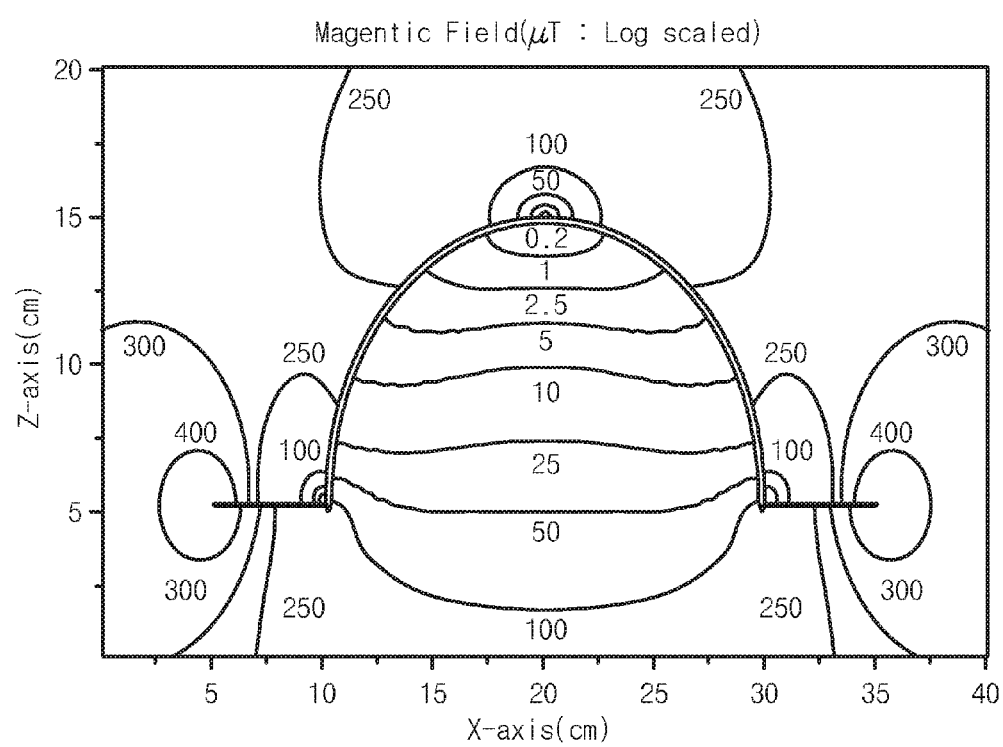
FIGS. 8A and 8B illustrate simulation results of contours of magnetic field intensity in a superconducting shielding helmet structure according to a brim type of a helmet.
Figure 8B:
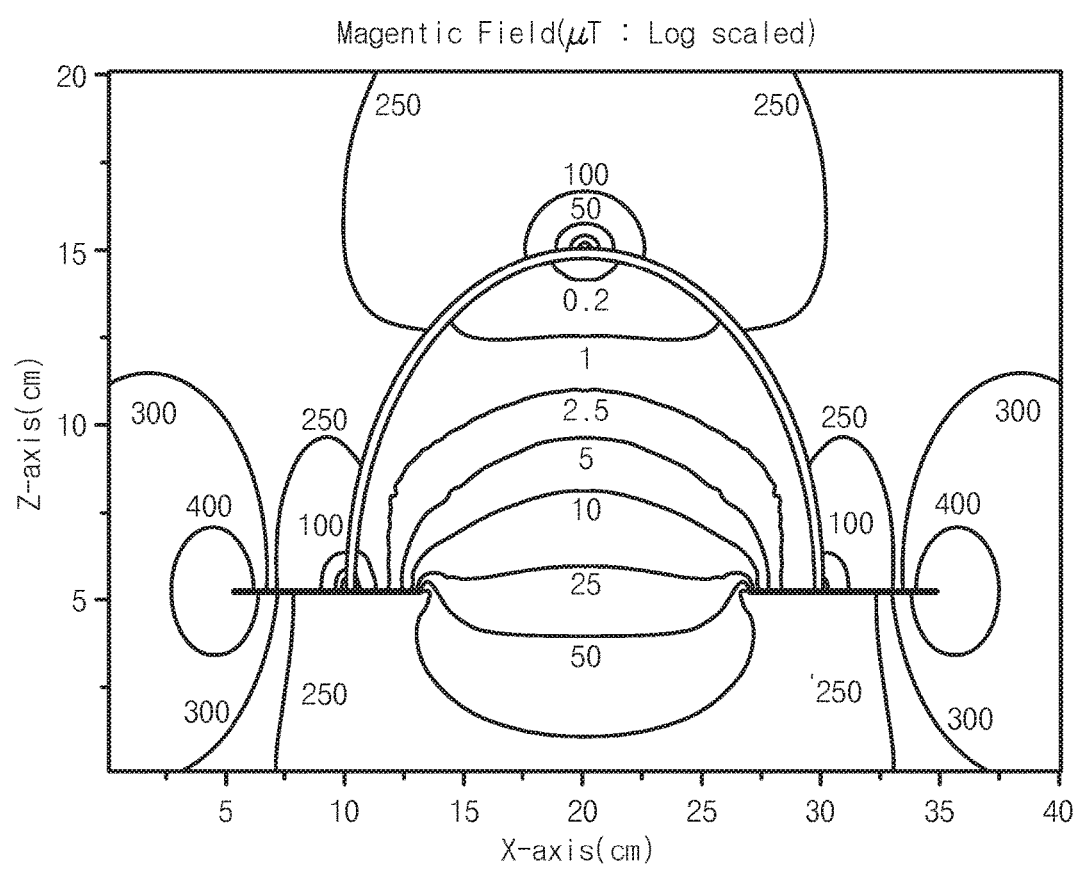

FIGS. 8A and 8B illustrate simulation results of contours of magnetic field intensity in a superconducting shielding helmet structure according to a brim type of a helmet.

Referring to FIGS. 6A through 8B, a helmet with an outward brim having width of 50 mm attached to only the outside of the helmet and a helmet with brims having widths of 50 mm and 30 mm attached to both sides (i.e., an outward brim and an inward brim) are certainly different in magnetic field distribution and magnetic-force line direction. When only the outward brim is formed, a magnetic field is focused toward the inner edge of the helmet and a magnetic field element perpendicular to, i.e., impinging on a surface of a pick-up coil was large.

When not only an outward brim but also an inward brim was inwardly formed by a distance (30 mm) at which the pick-up coil is spaced apart from a superconducting surface, it was confirmed that an angle formed by a magnetic field direction and the surface of the pick-up coil was made smaller. Preferably, length of the inward brim is 30 mm. Also preferably, length of the outward brim is 50 mm. When the length of the inward brim is equal to a spaced distance between the pick-up coil and the superconducting helmet, a magnetic field impinging on the pick-up coil may nearly horizontally imping on the surface of the pick-up coil. Thus, external magnetic noise may be reduced.

According to a modified embodiment of the present disclosure, a signal-to-noise ratio (SNR) when having only an inward brim was improved as compared to an SNR when having only an outward brim.

[Evaluation of System Noise Characteristics and Measurement of an Auditory Evoked Signal According to Shape of Helmet-Type Superconducting Shield]

Under the same environment, noise characteristics of SQUID systems were compared according to the shape of helmet-type superconducting shield. In addition, a signal-to-noise ratio (SNR) of an auditory evoked signal measured for the same measurement person was compared to confirm usefulness of a modified helmet-type MEG apparatus.

Figure 9:
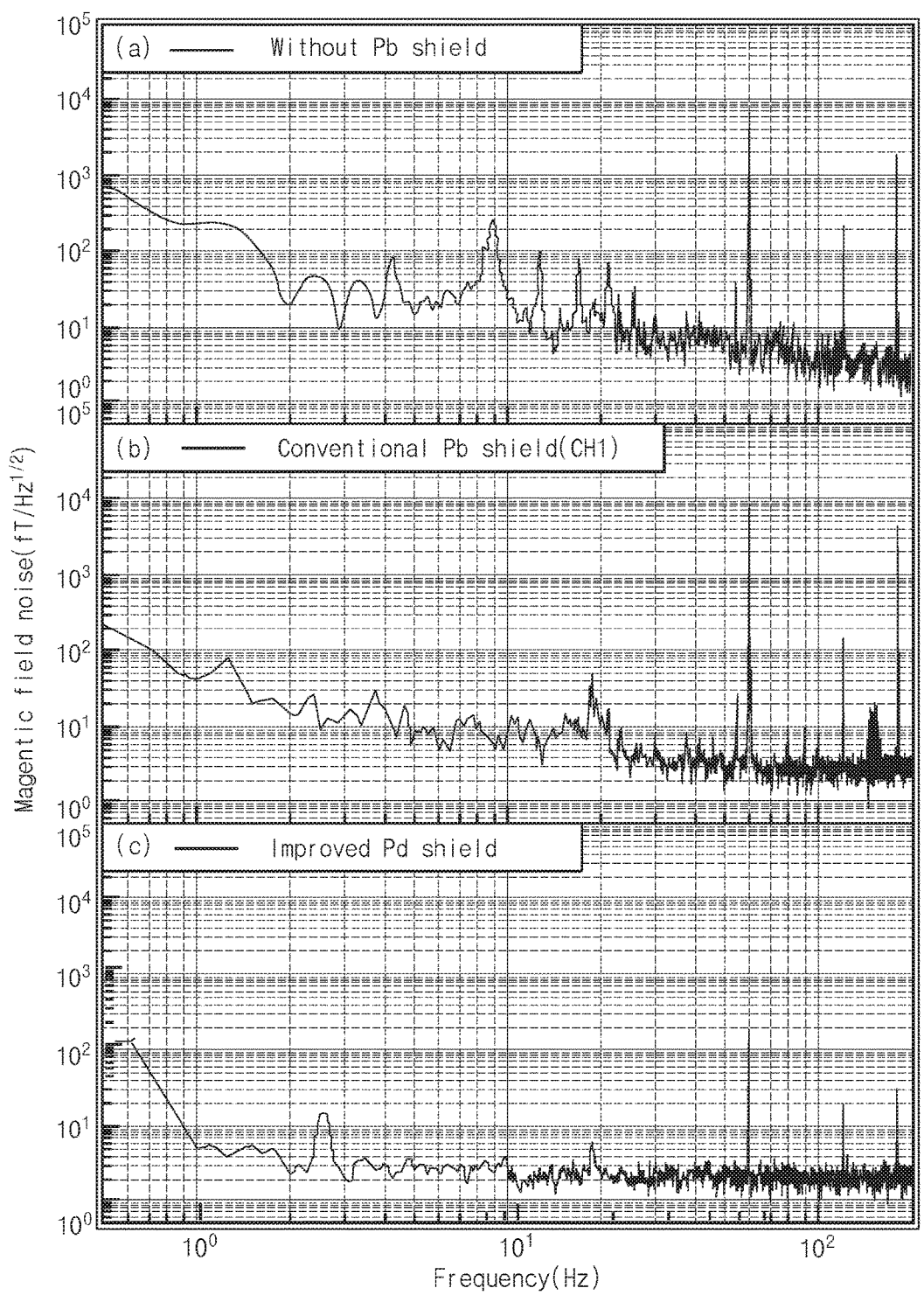
FIG. 9 illustrates noise characteristics of a magnetoencephalography (MEG) apparatus when there is no superconducting shield of a brim, when a brim is disposed only in an inward direction, and when a brim is disposed in both directions.

FIG. 9 illustrates noise characteristics of a superconducting helmet-type magnetoencephalography (MEG) apparatus depending on whether superconducting shield exists and a shape of a brim.

In a frequency region of 30 Hz or less, it was confirmed that noise was lowered when there are superconducting shields (b) and (c) as compared to when there is no superconducting shield (a). When having an outward brim, white noise of ~2 $fT/Hz^{1/2}$ appeared at a vertex having a relatively high superconducting factor and a very excellent noise characteristic of 7 $fT/Hz^{1/2}$ was exhibited in a low frequency region (1 Hz). However, power line noise measured at the edge of a helmet was 60 Hz noise of 5 to 7 $pT/Hz^{1/2}$ which was larger three to four times than noise of a gradiometer having a base line of 50 mm, and a noise level in a low-frequency region was 10 to 90 $fT/Hz^{1/2}$ which greatly varied depending on a position.

In the vicinity of the vertex of the helmet, a case of having an outward brim and an inward brim (c) exhibited a result similar to a case of having only the outward brim. However, at the edge of the helmet, noise of a low frequency (10 Hz or less) was significantly improved (5 to 10 $fT/Hz^{1/2}$). In addition, 60 Hz power line noise was reduced about 10 times as compared to the case of having only the outward brim.

By using the fabricated two types of inserts for measuring MEG (superconducting shield of an outward brim and superconducting shield of a bidirectional brim), a response signal for auditory stimulus evocation was measured with respect to a healthy man.

Figure 10:
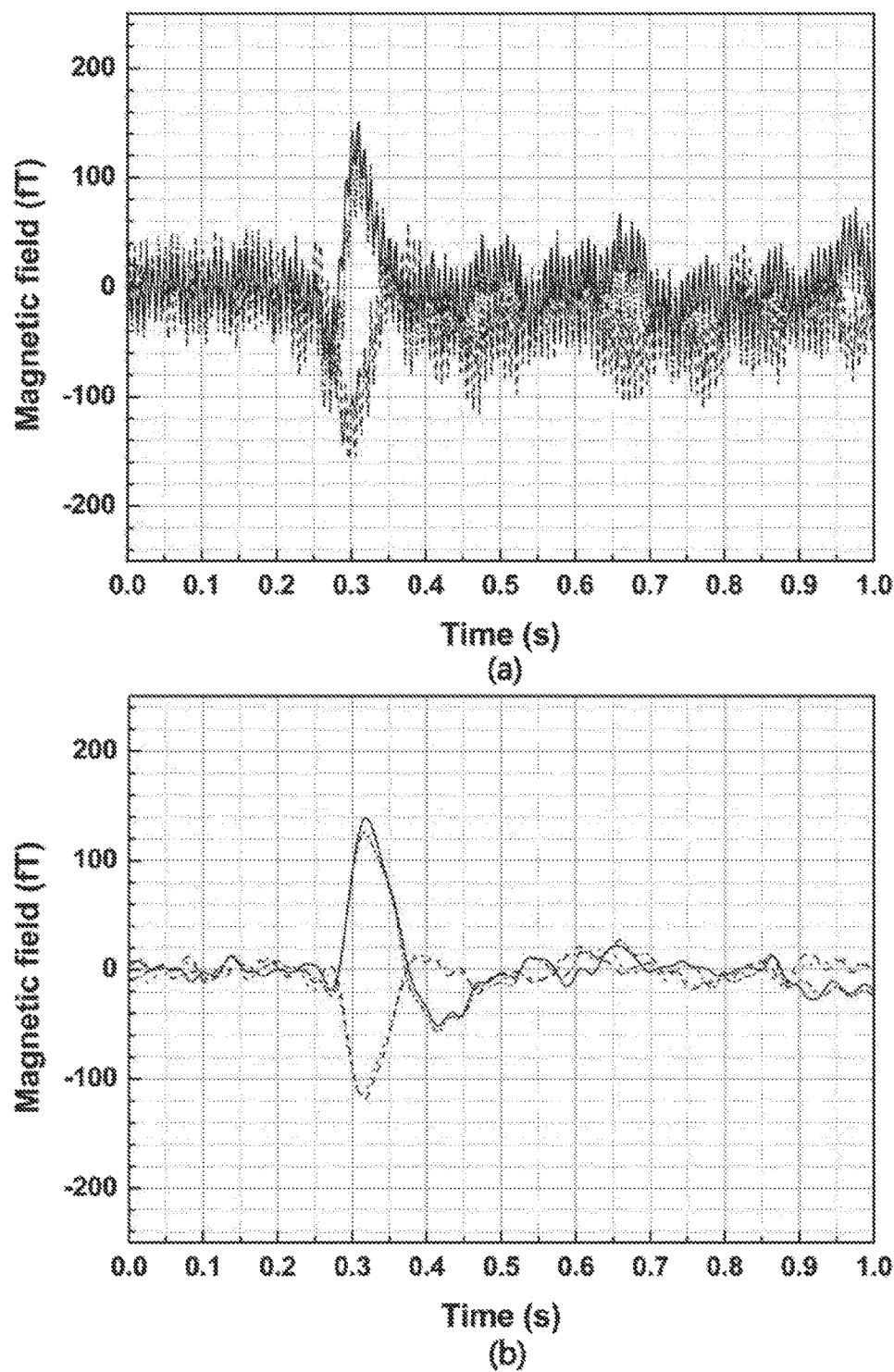
FIG. 10 illustrates addition averages obtained through 100-times measurement of an MEG signal evoked when an auditory stimulus is applied.

FIG. 10 illustrates addition averages obtained through 100-times measurement of an MEG signal evoked when an auditory stimulus is applied.

Referring to FIG. 10, it was difficult to analyze an auditory evoked signal measured by an MEG apparatus of a superconducting helmet having an outward brim although large 60 Hz power line noise and a single generated by low-frequency noise vibration are addition-averaged 100 times. However, an MEG apparatus using helmet-type superconducting shield having a bidirectional brim might measure a clear auditory signal of P50 and N100 and a signal-to-noise ratio (SNR) that is easy to analyze a signal was exhibited. It was confirmed that accordingly, a brim was bidirectionally formed in the helmet-type MEG apparatus using superconducting shield to measure an MEG signal more easily.

Since the intensity of a magnetic signal from a magnetic field signal source decreases in inverse proportion to the square of a distance, a distance between the signal source and a pick-up coil needs to be minimized to improve an SNR. A study was conducted on this method to develop and use a coil-in-vacuum SQUID where a pick-up coil is disposed in a vacuum vessel.

In a CIV-type SQUID apparatus, a pick-up coil and a SQUID sensor are disposed to be maintained in a vacuum state. Thus, only a low-temperature refrigerant exists in a helium inner storage container for storing a liquid refrigerant. Thus, there is only a path to fill the refrigerant. Thus, a diameter of a neck portion of the helium inner storage container may be significantly reduced. As a result, an evaporation rate of the liquid refrigerant may be reduced.

In a conventional CIV-type SQUID apparatus, a SQUID sensor and a pick-up coil are connected while being spaced apart from each other to prevent distortion of a magnetic signal. According to this method, manufacturing of the SQUID sensor has a high level of difficulty and maintenance is made difficult after the manufacturing of the SQUID sensor. Moreover, there is the disadvantage that a thermal transfer medium for cooling the pick-up coil must be additionally mounted. A SQUID sensor and a pick-up coil used in the conventional CIV-type SQUID apparatus are combined using a superconducting bolt and a superconducting nut. When the bulky superconducting bolt and nut approach the pick-up coil, a magnetometer measures a distorted magnetic signal. The magnetometer is not capable of accurately measure a signal desired to be measured because a balance factor is significantly reduced. In addition, a low SNR and great signal distortion may cause an important signal source localization error.

In view of the above, the conventional CIV-type SQUID apparatus uses a method for physically separating and fixing the SQUID sensor and the pick-up coil. A fixed position of the SQUID sensor is a position where the low-temperature refrigerant is attached to a bottom or sidewall, and the pick-up coil is fixed to a position adjacent to the signal source. This method suffers from the disadvantage that difficulty in manufacturing of the SQUID sensor and difficulty in combination of a low-temperature refrigerant storage container and the SQUID sensor increase significantly and thus much time and cost are required.

When a conventional CIV SQUID system is used in an MEG apparatus, other problems occur, as follows. A pick-up coil for measuring a biomagnetic signal using a SQUID sensor may be in the form of a magnetometer or a gradiometer.

The magnetometer measures an absolute value of a magnetic field to simultaneously measure a signal source and a neighboring great environmental noise. Thus, SQUID operating characteristics and a signal-to-noise ratio (SNR) greatly vary depending on the neighboring environmental noise. Particularly, in case of an MEG having a very weak signal, a special magnetically shielded room having a very high shielding factor is required.

The gradiometer includes a reference coil and a signal coil. The reference coil and the signal coil are wound in different directions. Thus, the gradiometer measures a differential value of a magnetic signal. Thus, uniform external environmental noise may be almost removed and a magnetic signal generated by a signal source adjacent to the signal coil may be relatively less offset to increase an SNR. If the gradiometer is used, a signal having a high SNR may be obtained in a magnetically shielded room having a lower shielding factor than the magnetometer. However, since length of the gradiometer is much greater than that of the magnetometer, an area occupied by a helmet-type gradiometer apparatus increase. Thus, an area in which radiant heat is received from room temperature also increases, which causes an evaporation rate of a low-temperature refrigerant to significantly increase. Accordingly, there is a need for a CIV MEG apparatus in which a distance between a pick-up coil and a signal source is short while using a magnetometer.

Assuming that a CIV SQUID system is applied to an MEG apparatus using a superconducting shield, a conventional helmet-type superconducting shield is introduced at a helmet edge in a direction of a magnetic force line perpendicular to a detection coil. The helmet-type superconducting shield significantly increases a noise level of a SQUID sensor disposed to be farthest from a vertex. Measurement of an MEG signal generated at an auditory cortex and a visual cortex is greatly limited. Thus, when the superconducting shield is used, a magnetometer may operate similarly to a gradiometer. Nonetheless, if the superconducting shield is used, it is difficult to measure the MEG signal generated at the auditory cortex and the visual cortex. Accordingly, there is a need for superconducting shield having a novel structure.

Figure 11A:
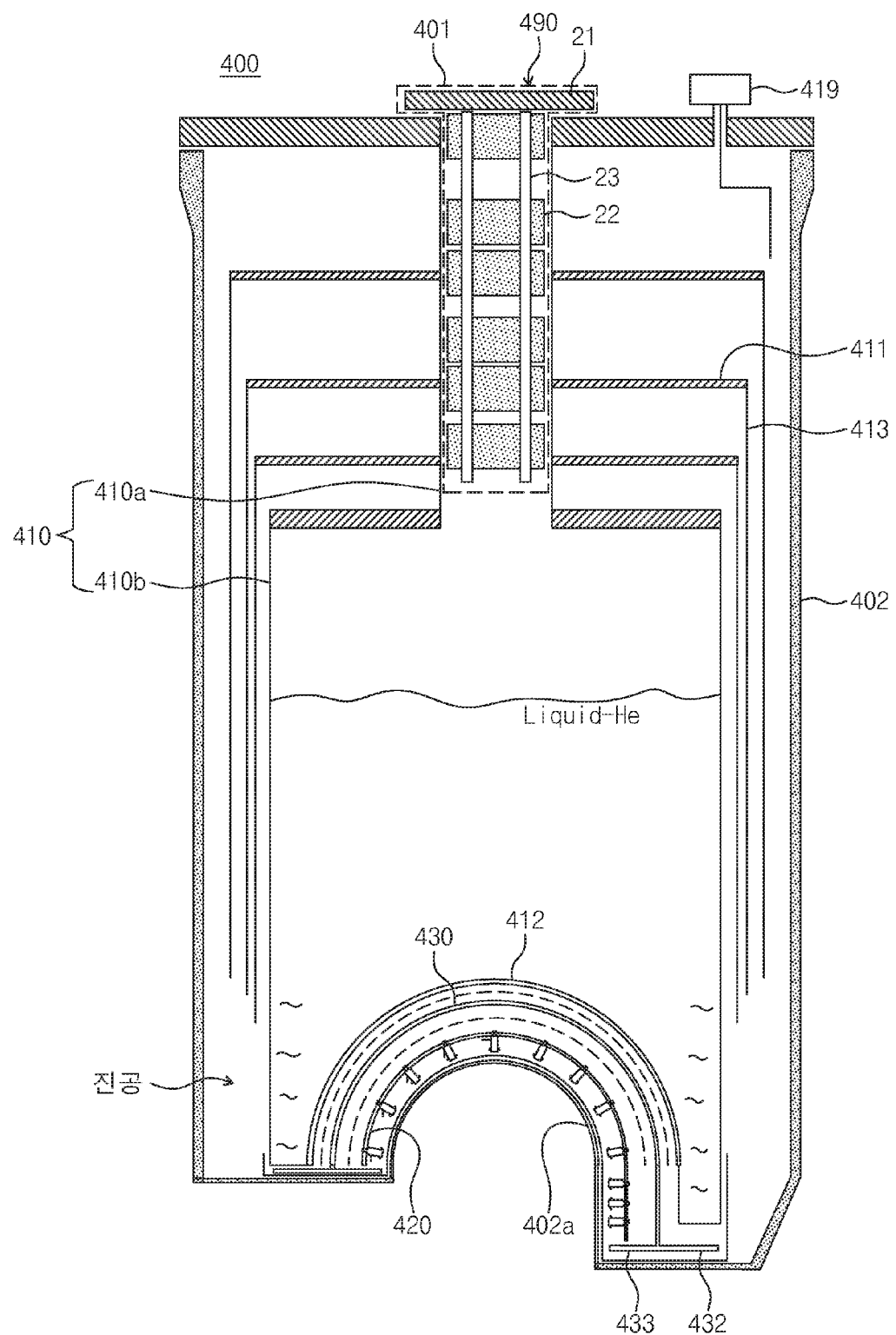
FIG. 11A illustrates an indirect cooling type magnetoencephalography (MEG) measuring apparatus in which a magnetometer and a superconducting shielding helmet are mounted in vacuum according to another example embodiments of the present disclosure.

FIG. 11A illustrates an indirect cooling type magnetoencephalography (MEG) measuring apparatus in which a magnetometer and a superconducting shielding helmet are mounted in vacuum according to another example embodiments of the present disclosure.

Figure 11B:
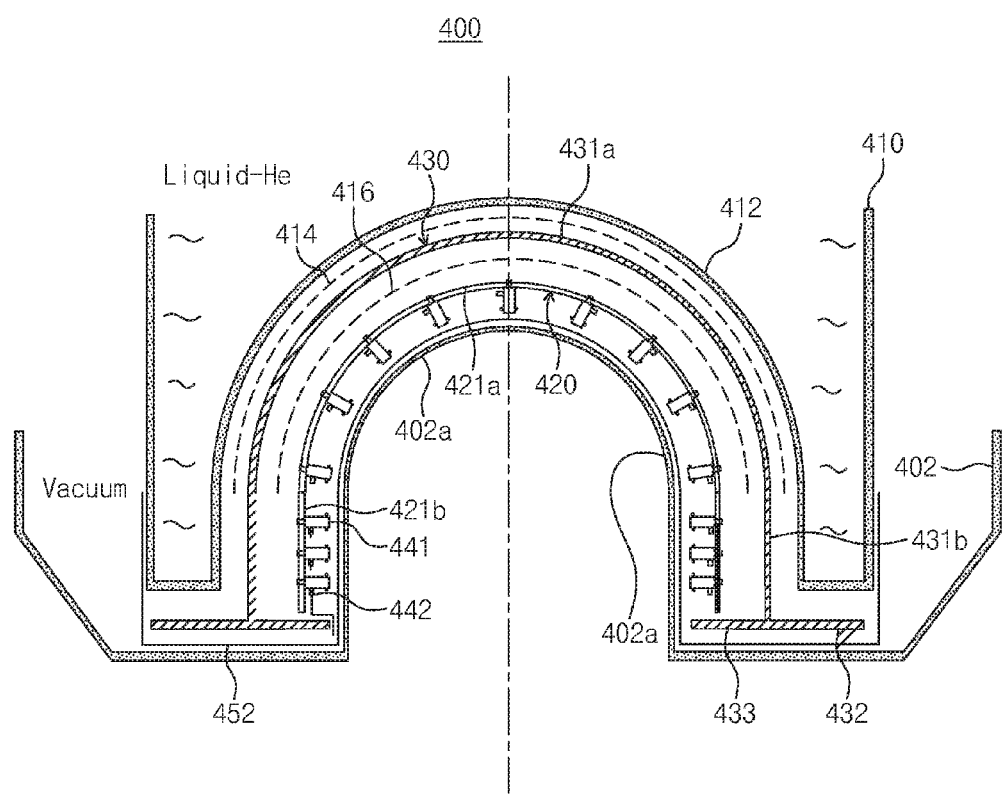
FIG. 11B is an exploded cross-sectional view of a superconducting helmet in FIG. 11A.

FIG. 11B is an exploded cross-sectional view of a superconducting helmet in FIG. 11A.

Figure 11C:
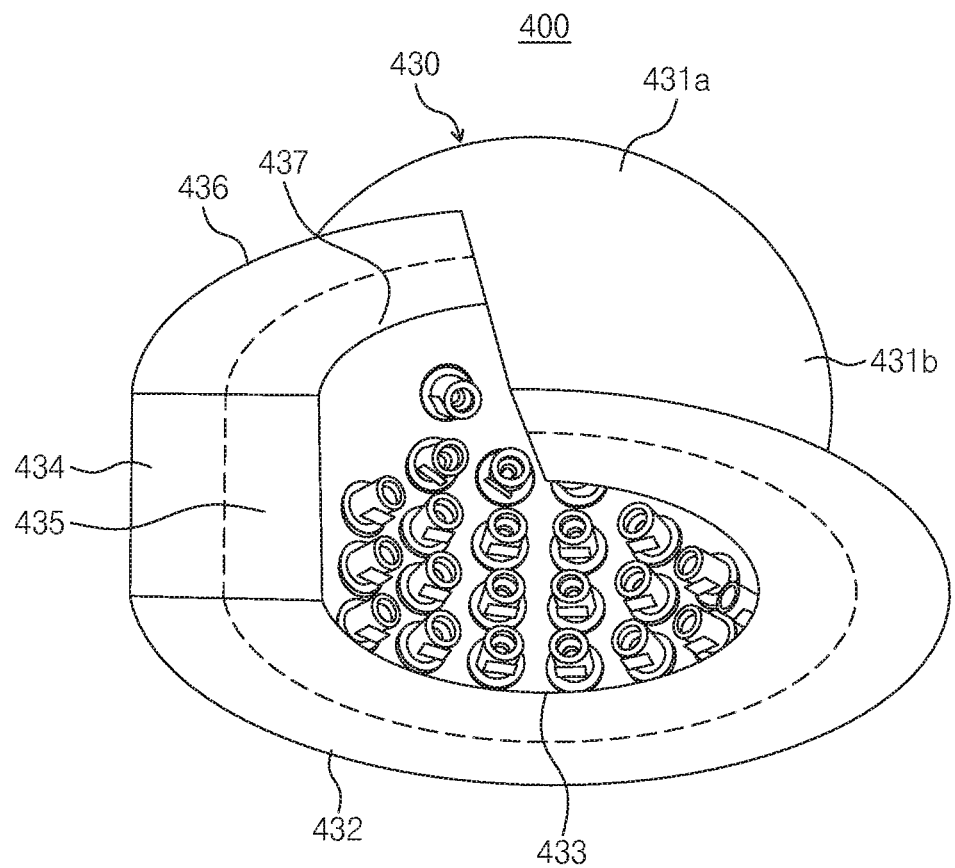
FIG. 11C is a perspective view of a superconducting helmet in FIG. 11A.

FIG. 11C is a perspective view of a superconducting helmet in FIG. 11A.

Figure 11D:
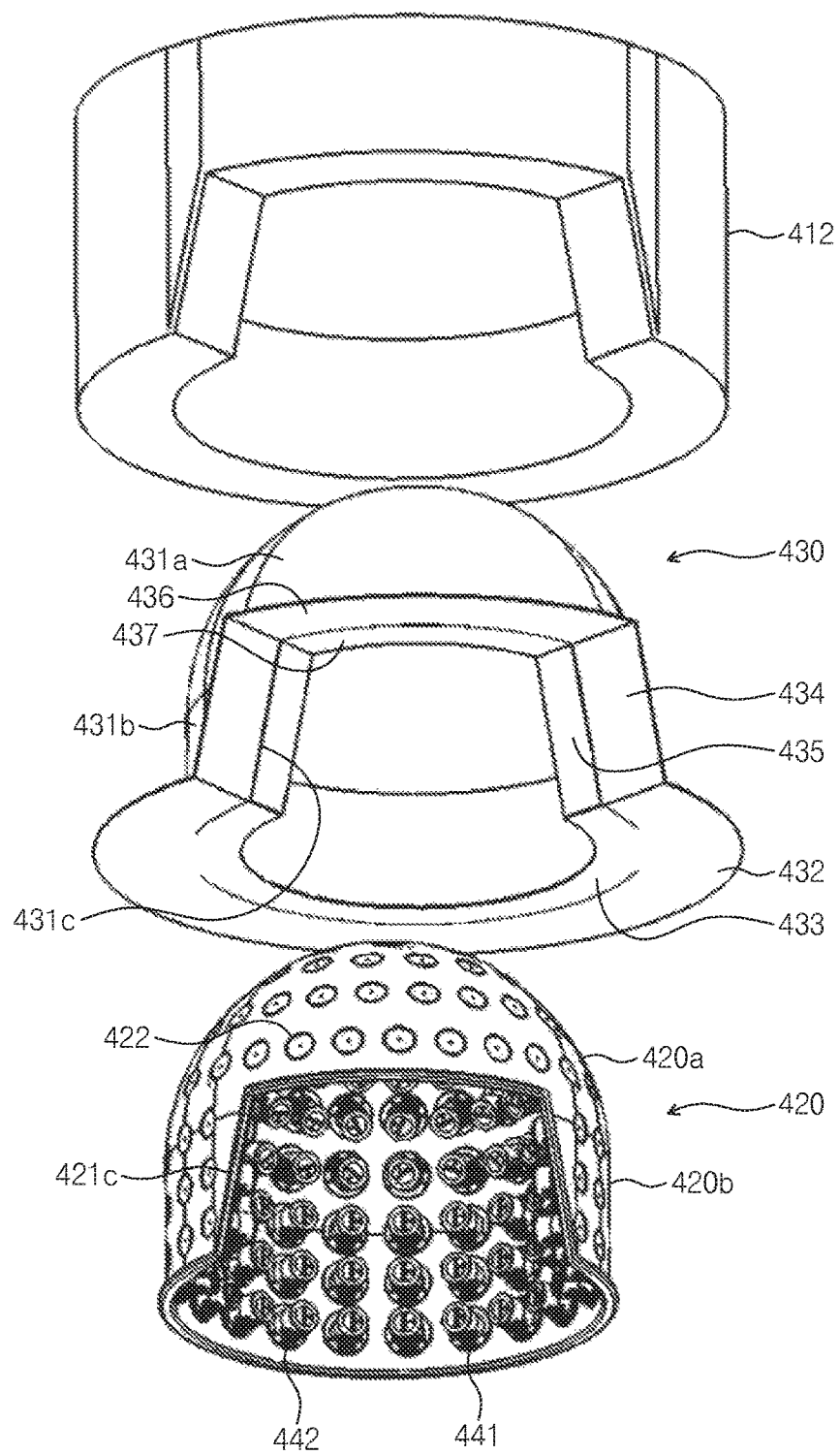
FIG. 11D is an exploded perspective view of the superconducting helmet in FIG. 11A.

FIG. 11D is an exploded perspective view of the superconducting helmet in FIG. 11A.

Figure 11E:
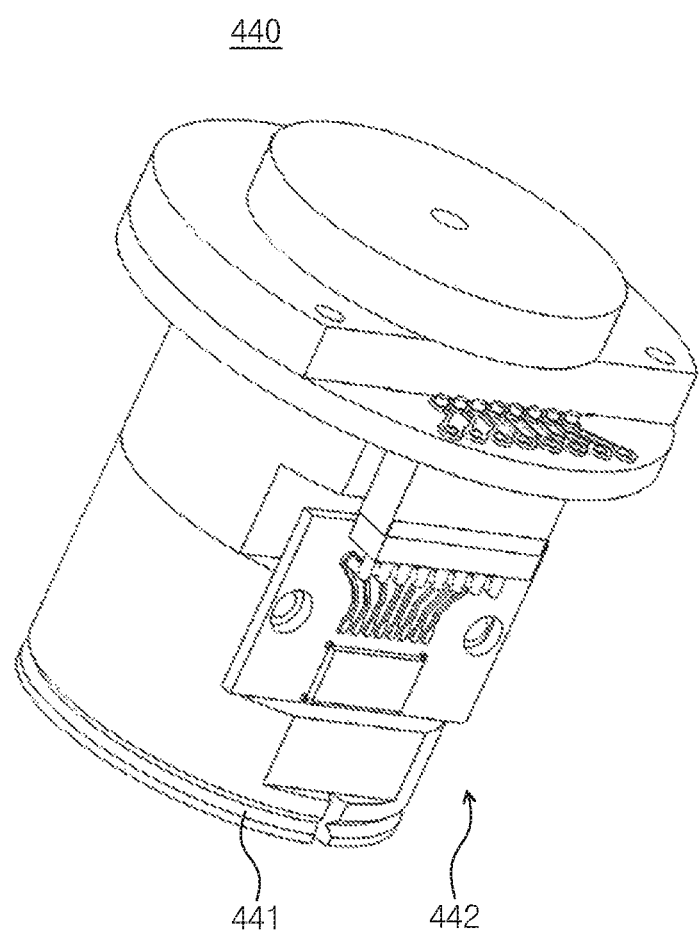
FIG. 11E is a combined perspective view of a SQUID sensor module in FIG. 11A.

FIG. 11E is a combined perspective view of a SQUID sensor module in FIG. 11A.

Figure 11F:
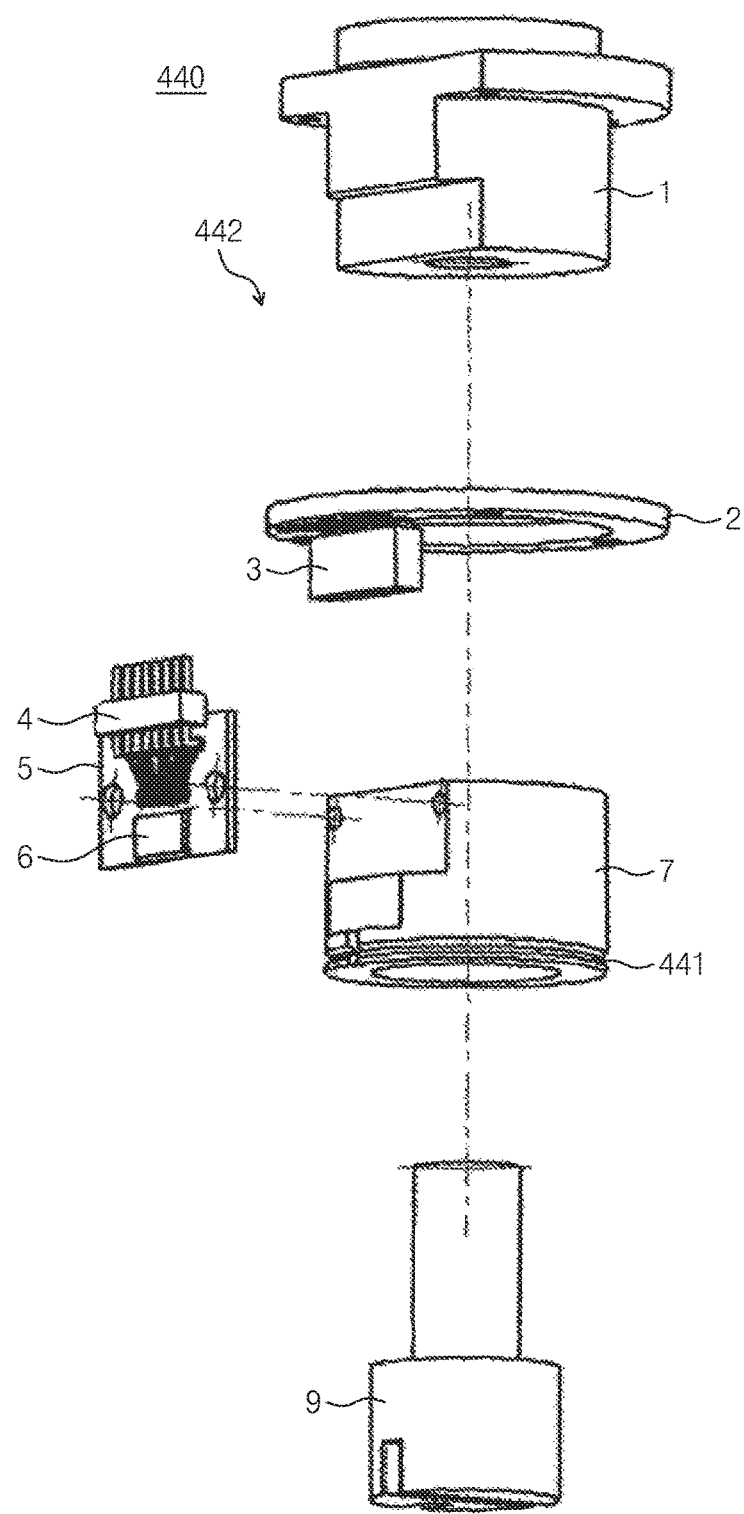
FIG. 11F is an exploded perspective view of the SQUID sensor module in FIG. 11E.

FIG. 11F is an exploded perspective view of the SQUID sensor module in FIG. 11E.

Referring to FIGS. 11A through 11F, a magnetoencephalography (MEG) measuring apparatus 400 includes a superconducting helmet 430 having an inward brim and an outward brim, a sensor-equipped helmet 420 disposed between the superconducting helmet 430 and an outer helmet 402a, a pick-up coil disposed in a space between the superconducting helmet 430 and the external helmet 402a, and a superconducting quantum interference device (SQUID) sensor 442 mounted on the sensor-equipped helmet 420 and connected to the pick-up coil 441. A SQUID magnetometer is completed by combining the pick-up coil 441 with the SQUID sensor 442.

A Dewar may include an outer container 402 and an inner container 410. The Dewar may have a coaxial cylindrical structure. A space between the outer container 402 and the inner container 410 is maintained in a vacuum state. The inner container 410 may include a top plate. A through-hole may be formed in the center of the top plate. The outer container 402 may be in the form of a cylinder. The outer helmet 402a may be disposed on a bottom surface of the outer container 402 to allow a person's head to be inserted.

The inner container 410 may include a neck portion 410a having a small diameter and a body portion 410b having a large diameter. The neck portion 410a and the body portion 410b may be in the form of a cylinder. An inner helmet 412 aligned with the outer helmet 402a may be disposed on a bottom surface of the body portion 410b.

A washer-shaped support portion 411 may be disposed on an outside surface of the neck portion 410a of the inner container 410. A thermal shielding portion 413 may be disposed on an outer circumferential surface of the support portion 411. The thermal shielding portion 413 may include an upper cylindrical portion and a lower slit portion successively combined with the upper cylindrical portion. The lower slit portion may have a slit formed in a vertical direction. The thermal shielding portion 413 may be made of a conductive material. A liquid refrigerant may be stored in the inner container 410. The thermal shielding portion 413 may include multiple layers to reduce a temperature gradient in vacuum. The thermal shielding layer 413 may include an aluminum-coated Mylar layer and a copper layer that are sequentially stacked to block radiant heat. The thermal shielding portion 413 may block introduction of external radiant heat.

An insert 401 may be inserted into the neck portion 410a of the inner container 410 to perform an adiabatic function. The insert 401 may include an insert top plate 21, a guide rod 23 combined with the insert top plate 21 and extending vertically, and an insert baffle 22 inserted into the guide rod 23.

The insert top plate 21 may be in the form of a disc and be made of G-10 epoxy. The insert top plate 21 may be fixed to a top plate of the outer container 302.

The guide rod 23 may be made of G-10 epoxy and be in the form of a rod or a pipe. The guide rod 23 may be means for supporting the insert baffle 22.

The insert baffle 22 may include a Styrofoam with superior warmth retention and a conductive plate. The conductive plate may include an aluminum-coated Mylar layer and a copper layer. The insert baffle 12 may block external thermal conductivity and influx of radiant heat.

A space between the inner container 410 and the outer container may be maintained in a vacuum state. The sensor-equipped helmet 420 and the superconducting helmet 430 disposed on the sensor-equipped helmet 420 may be disposed between the outer helmet 402a and the inner helmet 412. Thus, the outer helmet 402a, the sensor-equipped helmet 420, the superconducting helmet 430, and the inner helmet 412 may be sequentially disposed. The inner helmet 412 may fix and cool the sensor-equipped helmet 420.

A connector box 419 electrically connects the SQUID sensor 442 to an external circuit. The connector box 419 may connect a wiring extending through a vacuum portion to the external circuit and be disposed on a top plate of the inner container 410.

The sensor-equipped helmet 420 includes a spherical portion 421a and a cylindrical straight portion 421b successively connected to the spherical portion 421a. The straight portion 421b may be partially removed in a direction that a person' eye views. A plurality of through-holes 422 may be formed at the straight portion 421b and the hemispherical portion 421a of the sensor-equipped helmet 420. A SQUID sensor 442 is mounted in the through-hole 422.

The sensor-equipped helmet 420 may be made of G-10 epoxy and be fabricated with a plurality of components using an epoxy adhesive. The hemispherical portion 321a may have a hemispherical shape. The shape of the hemispherical portion 421a may be variously modified into, for example, a parabolic shape or an elliptical shape allowing a person's head to be inserted. The straight portion 421b may be successively connected to the hemispherical portion 421a. Accordingly, the straight portion 421b may have a cylindrical shape. An azimuthal element of the straight portion 421b may be partially removed to provide a visual field ensuring portion 431c. Specifically, an azimuthal element having the range between 45 and 180 degrees may be removed. Thus, a person's eye may ensure a visual field when the person's head is inside the sensor-equipped helmet 420.

The superconducting helmet 430 includes an inward brim 433, an outward brim 432, a hemispherical portion 431a, a cylindrical straight portion 431b successively connected to the hemispherical portion 431a, and a visual field ensuring portion 431c formed by partially removing the straight portion 431b. The superconducting helmet 430 may further include an inward side brim 435 disposed at opposite sides of the visual field ensuring portion 431c and connected to the inward brim 433, an outward side brim 434 disposed at opposite sides of the visual field ensuring portion 431c and connected to the outward brim 432, an inward upper brim 437 disposed on the visual field ensuring portion 431c and connected to the inward side brim 435, and an outward upper brim 436 disposed on the visual field ensuring portion 431c and connected to the outward side brim 334. The superconducting helmet 430 may shield external magnetic noise.

The inward brim 433, the inward side brim 435, and the inward upper brim 437 may be successively connected. The outward brim 432, the outward side brim 434, and the outward upper brim 436 may be successively connected. Length or width of the inward brim 433 may be 20 to 40 mm Length or width of the outward brim 432 may be 40 to 60 mm. A material of the superconducting helmet 430 may be lead (Pb). The superconducting helmet 430 may be fabricated by folding a plate. The superconducting helmet 430 may be formed using a mold. A vertically spaced distance between a surface of the superconducting helmet 430 and the pick-up coil 441 may be 20 to 40 mm. The vertically spaced distance may be equal to the length of the inward brim 433. In this case, an MEG signal generated at an auditory cortex and a visual cortex may be measured.

A first thermal conduction layer 414 may be disposed between the inner helmet 412 and the superconducting helmet 430 to transfer heat between the inner helmet 412 and the superconducting helmet 430. Thus, the superconducting helmet 430 may be cooled to a low temperature. A second thermal conduction layer 416 may be disposed between the superconducting helmet 430 and the sensor-equipped helmet 420 to transfer heat between the superconducting helmet 430 and the sensor-equipped helmet 420. Thus, the sensor-equipped helmet 420 and the SQUID sensor module 440 may be cooled to a low temperature. The first thermal conduction layer 414 and the second thermal conduction layer 416 may be made of a conductive mesh.

A thermal cap 452 may be made of a material having high thermal conductivity and increase cooling efficiency of the sensor module 440. The thermal cap 452 may be disposed between the sensor-equipped helmet 420 and the outer container 402. The thermal cap 452 may be disposed to cover the sensor-equipped helmet 420. The thermal cap 452 may be thermally connected to the lower end of a body portion 410b of the inner container 410. The thermal cap 452 may be a copper mesh for thermal conduction and an aluminum-coated thin Mylar material for thermal reflection.

The pick-up coil 441 may be a magnetometer. The pick-up coil 441 may include a bobbin 7 where a groove is formed to wind a coil. The bobbin 7 may be fixed to the sensor-equipped helmet 420 by a fixing block 1.

The SQUID sensor module 440 may include a SQUID printed circuit board (PCB) 5 on which a SQUID 6 is mounted, the bobbin 7 where a groove is formed to wind the pick-up coil 441, the fixing block 1 adapted to fix the bobbin 7, a signal wire connection PCB 2 adapted to control the SQUID 6 and transmit a detected signal to an external circuit, and a bobbin fixing bolt 9. The signal connection PCB 2 is connected to the SQUID PCB 5 to be separated therefrom or combined therewith by using a first connector 3 mounted on the signal wire connection PCB 2 and a second connector mounted on the SQUID PCB 5.

The SQUID PCB 5 electrically connects the SQUID 6 using eight bonding pad patterns. The SQUID PCB 5 is fixed to the bobbin 7 on which the pick-up coil 441 is wound, by using a non-metal bolt.

The pick-up coil 441 and an input coil of the SQUID 6 are directly connected to each other using a thermally processed superconducting line, and a SQUID magnetometer of an integrated shape is fabricated.

The fixing block 1 is mounted on the sensor-equipped helmet 420 to align and fix the SQUID sensor 442. For electric connection with an external circuit, the fixing block 1 supports a wire connection PCB 2 to an external circuit and an attachable structure is formed at the fixing block 1. Eight holes are formed at the wire connection PCB 2, and eight strands of power and signal line connected from the connector box 419 are connected to the eight holes. The wire connection PCB 2 may include a first pin connector 3 that may be in electrical contact with the SQUID PCB 5 to which a SQUID is attached.

The bobbin 7 of the SQUID sensor 442 to which the pick-up coil 441 is attached is combined with the fixing block 1 using a bobbin fixing bolt 9. In this case, the electrical connection is achieved through a second pin connector 4 of the SQUID PCB 5 and the first pin connector 3 attached to the wire connection PCB 2. Each SQUID 6 may very easily replace a SQUID of a bad channel by combining or separating a fixing bolt.

At least 100 SQUID magnetometer are used to measure and analyze an MEG signal, and spaces between the SQUID magnetometers are optimally maintained to avoid duplicate signal detection.

A CIV-type Dewar may significantly reduce a cross-sectional area of a Dewar neck as compared to a direct cooling type Dewar where a SQUID is submerged in liquid helium to be cooled. Thus, the CIV-type Dewar has an advantage to significantly decrease consumption of a high-priced low-temperature refrigerant. However, when a primary differential SQUID sensor is used, a thermal introduction area in a helmet greatly increases, which causes an evaporation rate of the low-temperature refrigerant to increase.

A superconducting helmet was used in a CIV-type MEG to overcome the above disadvantage. When a SQUID magnetometer is shielded with a superconductor, the SQUID magnetometer has the same operating characteristics as the SQUID gradiometer. If the characteristics are applied to a CIV-type MEG apparatus, a surface area of a vacuum vessel helmet where a SQUID sensor module is disposed may decrease by 40 percent. A surface area of a thermal shield layer exposed to an absolute temperature of 300 K may decrease by 290 percent as compared to a CIV-type MEG apparatus including a gradiometer. Thus, thermal leakage from a lower end of a low-temperature coolant storage container may be significantly reduced. Specifically, when the integrated magnetometer is used, a distance between an outer helmet and an inner helmet decreases as length of the bobbin decreases. On the other hand, an area of a bottom surface between the inner helmet and the outer helmet viewing a bottom surface of the external container maintained at room temperature decreases. As the area of the bottom surface decreases, thermal introduction through the area may be reduced to decrease a coolant evaporation rate.

A superconducting helmet having an inward brim allows an MEG signal generated at an auditory cortex and a visual cortex to be easily measured. Since the superconducting helmet having the inward brim may shield magnetic nose of all frequency bands, miniaturization and weight reduction of a magnetically shielded room may be achieved.

A superconducting shield according to the present disclosure was applied to a 152-channel MEG SQUID apparatus. An auditory evoked signal and a visual evoked signal were measured with respect to a normal person by using the MEG SQUID apparatus to which the present disclosure is applied.

A signal-to-noise ratio (SNR) of the measured signal was improved five or more times as compared to a normal superconducting shield.

As described above, an example embodiment of the present disclosure provides a magnetoencephalography (MEG) measuring apparatus equipped with a novel-shaped superconducting helmet. According to an example embodiment of the present disclosure, an MEG signal generated in the vicinity of a helmet edge such as an auditory cortex or a visual cortex may be measured.

Although the present disclosure and its advantages have been described in detail, it should be understood that various changes, substitutions and alterations can be made herein without departing from the spirit and scope of the disclosure as defined by the following claims.

What is claimed is:

1. A magnetoencephalography (MEG) measuring apparatus comprising:
    a superconducting helmet having an inward brim;
    a sensor-equipped helmet disposed inside the superconducting helmet;
    a pick-up coil disposed inside the sensor-equipped helmet; and
    a superconducting quantum interference device (SQUID) sensor mounted on the sensor-equipped helmet and connected to the pick-up coil.

2. The MEG measuring apparatus as set forth in claim 1, wherein the superconducting helmet, the sensor-equipped helmet, the pick-up coil, and the SQUID sensor are submerged in a liquid refrigerant to be directly cooled.

3. The MEG measuring apparatus as set forth in claim 1, wherein the pick-up coil is a magnetometer.

4. The MEG measuring apparatus as set forth in claim 1, wherein a width of the inward brim is 20 to 40 mm.

5. The MEG measuring apparatus as set forth in claim 1, wherein the superconducting helmet further comprises:
    an outward brim;
    a hemispherical portion;
    a cylindrical straight portion successively connected to the hemispherical portion; and
    a visual field ensuring portion where the straight portion is partially removed,
    the inward brim is disposed along an inner side surface from a bottom surface of the straight portion and is in the form of a washer removed in a direction of the visual field ensuring portion, and
    the outward brim is disposed along an outer side surface from the bottom surface of the straight portion and is in the form of the washer removed in the direction of the visual field ensuring portion.

6. The MEG measuring apparatus as set forth in claim 5, wherein the superconducting helmet further comprises:
    an inward side brim disposed at opposite sides of the visual field ensuring portion and connected to the inward brim;
    an outward side brim disposed at the opposite sides of the visual field ensuring portion and connected to the outward brim;
    an inward upper brim disposed on the visual field ensuring portion and connected to the inward side brim; and
    an outward upper brim disposed on the visual field ensuring portion and connected to the outward side brim.

7. The MEG measuring apparatus as set forth in claim 1, wherein a material of the superconducting helmet is lead.

8. The MEG measuring apparatus as set forth in claim 1, wherein the pick-up coil is disposed to have a constant vertical direction on an inner side of the sensor-equipped helmet, and
    the vertical direction is equal to a width of the inward brim.

9. A magnetoencephalography (MEG) measuring apparatus comprising:
    an inner container adapted to store a liquid refrigerant and including an inner helmet;
    an outer container including an outer helmet disposed to surround the inner helmet;
    a superconducting helmet disposed in a space between the inner helmet and the outer helmet and including an inward brim;
    a sensor-equipped helmet disposed in a space between the superconducting helmet and the outer helmet;
    a pick-up coil disposed in a space between the sensor-equipped helmet and the outer helmet; and
    a superconducting quantum interference device (SQUID) sensor mounted on the sensor-equipped helmet and connected to the pick-up coil,
    wherein a space between the inner container and the outer container is maintained in a vacuum state.

10. The MEG measuring apparatus as set forth in claim 9, wherein the pick-up coil is a magnetometer.

11. The MEG measuring apparatus as set forth in claim 9, wherein width of the inward brim is 20 to 40 mm.

12. The MEG measuring apparatus as set forth in claim 9, wherein the superconducting helmet further comprises:
    an outward brim;
    a hemispherical portion;
    a cylindrical straight portion successively connected to the hemispherical portion; and
    a visual field ensuring portion where the straight portion is partially removed;
    the inward brim being disposed along an inner side surface from a bottom surface of the straight portion and is in the form of a washer removed in a direction of the visual field ensuring portion, and
    the outward brim being disposed along an outer side surface from the bottom surface of the straight portion and is in the form of the washer removed in the direction of the visual field ensuring portion.

13. The MEG measuring apparatus as set forth in claim 9, wherein the superconducting helmet further comprises:
    an inward side brim disposed at opposite sides of the visual field ensuring portion and connected to the inward brim;
    an outward side brim disposed at the opposite sides of the visual field ensuring portion and connected to the outward brim;
    an inward upper brim disposed on the visual field ensuring portion and connected to the inward side brim; and
    an outward upper brim disposed on the visual field ensuring portion and connected to the outward side brim.

14. The MEG measuring apparatus as set forth in claim 9, wherein a spaced distance from an inner surface of a superconducting helmet to the pick-up coil is equal to the width of the inward brim.

15. The MEG measuring apparatus as set forth in claim 9, further comprising:
    a thermal cap disposed between the sensor-equipped helmet and the outer helmet.

16. A magnetoencephalography (MEG) measuring apparatus comprising:

a superconducting helmet having an inward brim;
a sensor-equipped helmet disposed inside the superconducting helmet;
a pick-up coil disposed inside the sensor-equipped helmet; and
a superconducting quantum interference device (SQUID) sensor disposed inside the sensor-equipped helmet.

* * * * *